United States Patent
Jacob et al.

(10) Patent No.: US 12,295,761 B2
(45) Date of Patent: May 13, 2025

(54) COLLIMATOR ASSEMBLY FOR AN X-RAY DETECTOR

(71) Applicant: GE Precision Healthcare LLC, Wauwatosa, WI (US)

(72) Inventors: Biju Jacob, Niskayuna, NY (US); Mark Adamak, Wauwatosa, WI (US); Brian Yanoff, Niskayuna, NY (US); Jonathan Short, Ballston Spa, NY (US); Bruno Kristiaan Bernard De Man, Clifton Park, NY (US); Katsumasa Nose, Tokyo (JP); Hengshan Gao, Tokyo (JP)

(73) Assignee: GE Precision Healthcare LLC, Wauwatosa, WI (US)

( * ) Notice: Subject to any disclaimer, the term of this patent is extended or adjusted under 35 U.S.C. 154(b) by 452 days.

(21) Appl. No.: 17/743,907

(22) Filed: May 13, 2022

(65) Prior Publication Data

US 2023/0363728 A1    Nov. 16, 2023

(51) Int. Cl.
*A61B 6/06* (2006.01)
*A61B 6/03* (2006.01)
*G21K 1/04* (2006.01)

(52) U.S. Cl.
CPC .............. *A61B 6/06* (2013.01); *A61B 6/032* (2013.01); *G21K 1/04* (2013.01)

(58) Field of Classification Search
CPC ......... A61B 6/06; A61B 6/032; A61B 6/4266; A61B 6/4291; A61B 6/035; A61B 6/44; G21K 1/04
See application file for complete search history.

(56) References Cited

U.S. PATENT DOCUMENTS

| | | | |
|---|---|---|---|
| 7,112,797 B2 | 9/2006 | Hoge | |
| 7,247,856 B2 | 7/2007 | Hoge | |
| 10,191,162 B2 | 1/2019 | Danielsson | |
| 10,610,191 B2 | 4/2020 | Sjolin | |
| 11,000,242 B1* | 5/2021 | Nose | A61B 6/4233 |
| 11,054,532 B2 | 7/2021 | Hjärn et al. | |
| 2012/0307963 A1 | 12/2012 | Watanabe | |
| 2020/0375554 A1* | 12/2020 | Ergler | A61B 6/06 |

FOREIGN PATENT DOCUMENTS

EP    2662023 A1    11/2013

OTHER PUBLICATIONS

EP application 23170920.5 filed May 1, 20203—extended Search Report issued Sep. 19, 2023; 7 pages.

* cited by examiner

*Primary Examiner* — David P Porta
*Assistant Examiner* — Meenakshi S Sahu

(57) ABSTRACT

There is provided an X-ray imaging system having an X-ray source, an X-ray detector and a collimator assembly in the X-ray path between the X-ray source and the X-ray detector. The X-ray detector comprises a plurality of detector modules arranged side-by-side and adapted to be oriented towards the X-ray source, the detector modules being arranged side-by-side along a direction substantially orthogonal to the direction of incoming X-rays. The collimator assembly is based on a plurality of spaced collimator plates arranged side-by-side in a direction coinciding with the direction of the detector modules. The collimator assembly further comprises a physically stabilizing lateral support structure arranged in a lateral plane extending in a direction substantially orthogonal to the direction of incoming X-rays.

19 Claims, 23 Drawing Sheets

COLLIMATOR ASSEMBLY FOR AN X-RAY DETECTOR

BACKGROUND

The proposed technology relates to X-ray technology and X-ray imaging. In particular, the proposed technology relates to an X-ray imaging system such as a Computed Tomography (CT) imaging system.

Radiographic imaging such as Computed Tomography (CT) imaging systems have been used for years in medical applications, such as for medical diagnostics and treatment.

Normally, an X-ray imaging system such as a CT imaging system includes an X-ray source and an X-ray detector consisting of multiple detector modules comprising one or many detector elements, for independent measuring of X-ray intensities. The X-ray source emits X-rays, which pass through a subject or object to be imaged and are then received by the X-ray detector. The X-ray source and X-ray detector are typically arranged to rotate on a rotating member of a gantry, around the subject or object. The emitted X-rays are attenuated by the subject or object as they pass through, and the resulting transmitted X-rays are measured by the detector. The measured data may then be used to reconstruct images of the subject or object.

It may be useful with a brief overview of an illustrative general X-ray imaging system according to the prior art with reference to FIG. 1A. In this illustrative example the X-ray imaging system 100 comprises an X-ray source 10, an X-ray detector 20 and an associated image processing system 30. In general, the X-ray detector 20 is configured to register radiation from the X-ray source 10, which optionally has been focused by optional X-ray optics or collimators and passed through an object, a subject or a part thereof. The X-ray detector 20 is connectable to the image processing system 30 via suitable analog read-out electronics, which is at least partly integrated in the X-ray detector 20, to enable image processing and/or image reconstruction by the image processing system 30. Optionally, a collimator assembly 70 may be arranged in the X-ray path between the X-ray source 10 and the X-ray detector 20.

By way of example, a conventional CT imaging system includes an X-ray source and an X-ray detector arranged in such a way that projection images of the subject or object can be acquired in different viewing angles covering at least 180 degrees. This is most commonly achieved by mounting the source and detector on a support, e.g., a rotating member of a gantry, that is able to rotate around the subject or object. An image containing the projections registered in the different detector elements for the different view angles is called a sinogram. In the following, a collection of projections registered in the different detector elements for different view angles will be referred to as a sinogram even if the detector is two-dimensional, making the sinogram a three-dimensional image.

FIG. 1B is a schematic diagram illustrating an example of an X-ray imaging system setup according to the prior art, showing projection lines from an X-ray source through an object to an X-ray detector.

A further development of X-ray imaging is energy-resolved X-ray imaging, also known as spectral X-ray imaging, where the X-ray transmission is measured for several different energy levels. This can be achieved by letting the source switch rapidly between two different emission spectra, by using two or more X-ray sources emitting different X-ray spectra, or by using an energy-discriminating detector which measures the incoming radiation in two or more energy levels. An example of such a detector is a multi-bin photon-counting detector, where each registered photon generates a current pulse which is compared to a set of thresholds, thereby counting the number of photons incident in each of a number of energy bins.

Many X-ray imaging systems are equipped with a post-patient collimator arranged in the X-ray path between the X-ray source and the X-ray detector, mainly to provide for rejection of scattered X-ray photons. The collimator assembly should preferably be easily manufactured, while providing sufficient scatter rejection and allowing good detection efficiency.

There is a general demand for improvements with regard to the design and/or configuration of collimator assemblies, and especially post-patient collimators, in X-ray imaging systems such as CT imaging systems.

SUMMARY

This summary introduces concepts that are described in more detail in the detailed description. It should not be used to identify essential features of the claimed subject matter, nor to limit the scope of the claimed subject matter.

It is general object to provide an improved collimator assembly in the context of an x-ray imaging system. It is a specific object to provide an improved X-ray imaging system. These and other objects are met by one or more embodiments of the present invention, as defined by the claims.

According to a first aspect there is provided an X-ray imaging system comprising an X-ray source, an X-ray detector and a collimator assembly coupled to the X-ray detector. The X-ray detector comprises a plurality of detector modules arranged side-by-side and oriented towards the X-ray source, the detector modules being arranged side-by-side along a direction substantially orthogonal to the direction of incoming X-rays. The collimator assembly includes a plurality of spaced apart collimator plates arranged side-by-side in a direction coinciding with the direction of the detector modules. The collimator assembly further comprises a physically stabilizing lateral support structure arranged in a lateral plane extending in a direction substantially orthogonal to the direction of incoming X-rays.

In this way, the collimator will be less sensitive to deformation caused by various forces occurring during operation of the X-ray imaging system, e.g., when performing a patient scan. In addition, the improvements with respect to rigidity allows the use of relatively tall collimator plates in the direction of the incoming x-rays, which in turn enables provision of sufficient scatter rejection.

By way of example, the X-ray imaging system may be a rotating Computed Tomography (CT), system.

The proposed technology offers one or more of the following advantages of the X-ray imaging system, including the collimator assembly, as will be understood by reference to the description of various exemplifying embodiments:

Improved rigidity;
Less complex manufacturing;
Sufficient scatter rejection;
Reduced deformation during operation;
Improved detection efficiency.

BRIEF DESCRIPTION OF THE DRAWINGS

The embodiments, together with further objects and advantages thereof, may best be understood by making reference to the following description taken together with the accompanying drawings.

DETAILED DESCRIPTION

Embodiments of the present disclosure will now be described, by way of example, with reference to the figures.

For a better understanding, it may be useful to continue with an introductory description of non-limiting examples of an overall X-ray imaging system in which data processing and transferring according to the inventive concept may be implemented.

Figure 2:
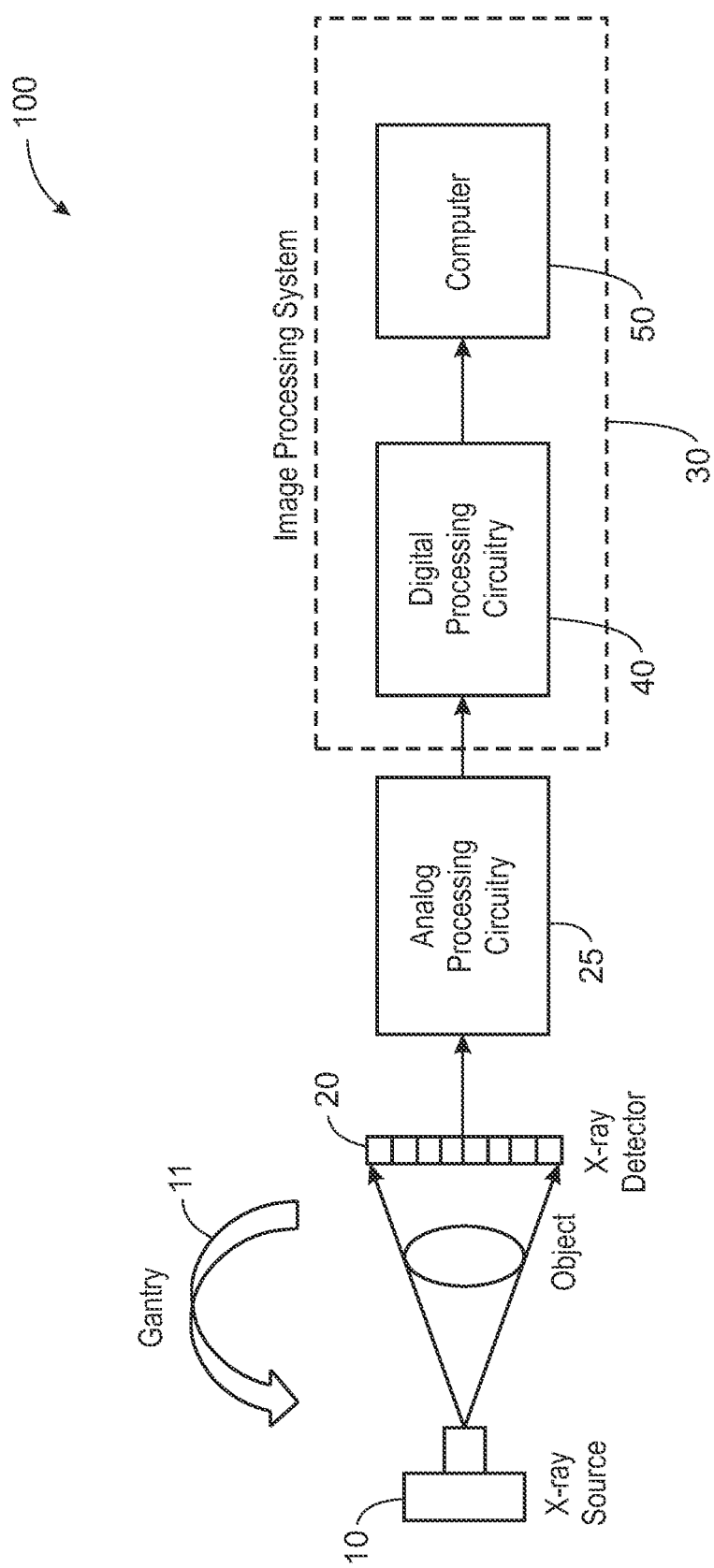
FIG. 2 is a schematic diagram illustrating another example of an X-ray imaging system, such as a CT imaging system.

FIG. 2 is a schematic diagram illustrating an example of an X-ray imaging system 100, such as a CT imaging system, comprising an X-ray source 10, which emits X-rays, an X-ray detector 20 with an X-ray detector, which detects X-rays after they have passed through the object, analog processing circuitry 25, which processes the raw electrical signals from the X-ray detector and digitizes it, digital processing circuitry 40, which may carry out further processing operations on the measured data, such as applying corrections, storing it temporarily, or filtering, and a computer 50, which stores the processed data and may perform further post-processing and/or image reconstruction. According to an exemplary embodiment, all or part of the analog processing circuitry 25 may be implemented in the X-ray detector 20. The X-ray source and X-ray detector may be coupled to a rotating member of a gantry 11 of the CT imaging system 100.

The overall X-ray detector may be regarded as the X-ray detector 20, or the X-ray detector 20 combined with the associated analog processing circuitry 25.

In communication with and electrically coupled to the analog processing circuitry 25 is an image processing system 30, which may include digital processing circuitry 40 and/or a computer 50, which may be configured to perform image reconstruction based on the image data from the X-ray detector. The image processing system 30 may, thus, be seen as the computer 50, or alternatively the combined system of the digital processing circuitry 40 and the computer 50, or possibly the digital processing circuitry 40 by itself if the digital processing circuitry is further specialized also for image processing and/or reconstruction.

An example of a commonly used X-ray imaging system is a CT imaging system, which may include an X-ray source or X-ray tube that produces a fan beam or cone beam of X-rays and an opposing array of X-ray detectors measuring the fraction of X-rays that are transmitted through a patient or object. The X-ray source or X-ray tube and X-ray detector are mounted in a gantry 11 that rotates around the imaged object.

Figure 3:
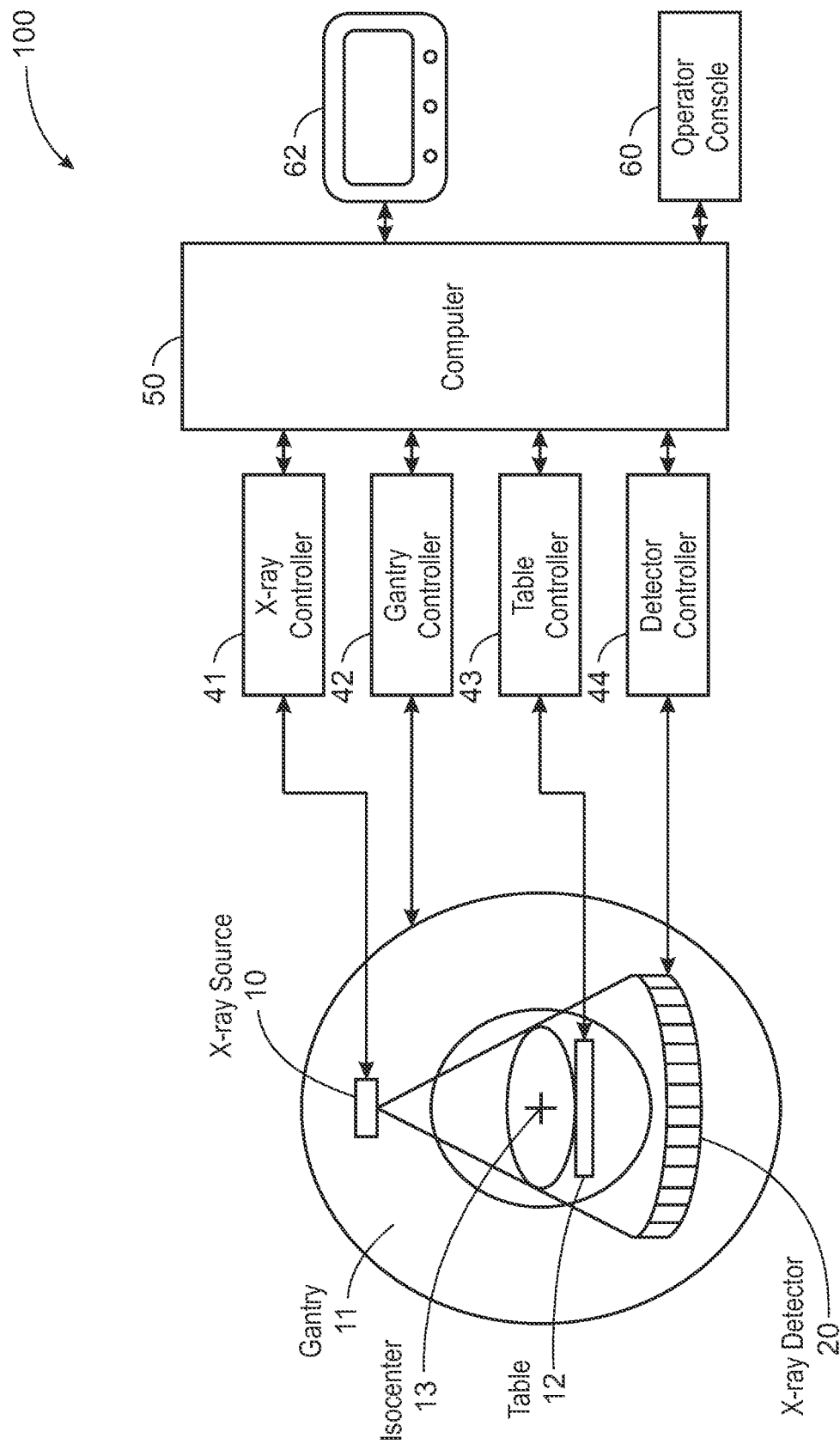
FIG. 3 is a schematic block diagram of a CT imaging system as an illustrative example of an X-ray imaging system.

FIG. 3 schematically shows a CT imaging system 100 as an illustrative example of an X-ray imaging system. The CT imaging system comprises a computer 50 receiving commands and scanning parameters from an operator via an operator console 60 that may have a display 62 and some form of operator interface, e.g., a keyboard, mouse, joy stick, touch screen or other input device. The operator supplied commands and parameters are then used by the computer 50 to provide control signals to an X-ray controller 41, a gantry controller 42 and a table controller 43. To be specific, the X-ray controller 41 provides power and timing signals to the X-ray source 10 to control emission of X-rays onto the object or patient lying on the table 12. The gantry controller 42 controls the rotating speed and position of the gantry 11 comprising the X-ray source 10 and the X-ray detector 20. By way of example, the X-ray detector 20 may be a photon-counting X-ray detector. The table controller 43 controls and determines the position of the patient table 12 and the scanning coverage of the patient. There is also a detector controller 44, which is configured for controlling and/or receiving data from the X-ray detector 20.

Figure 1A:
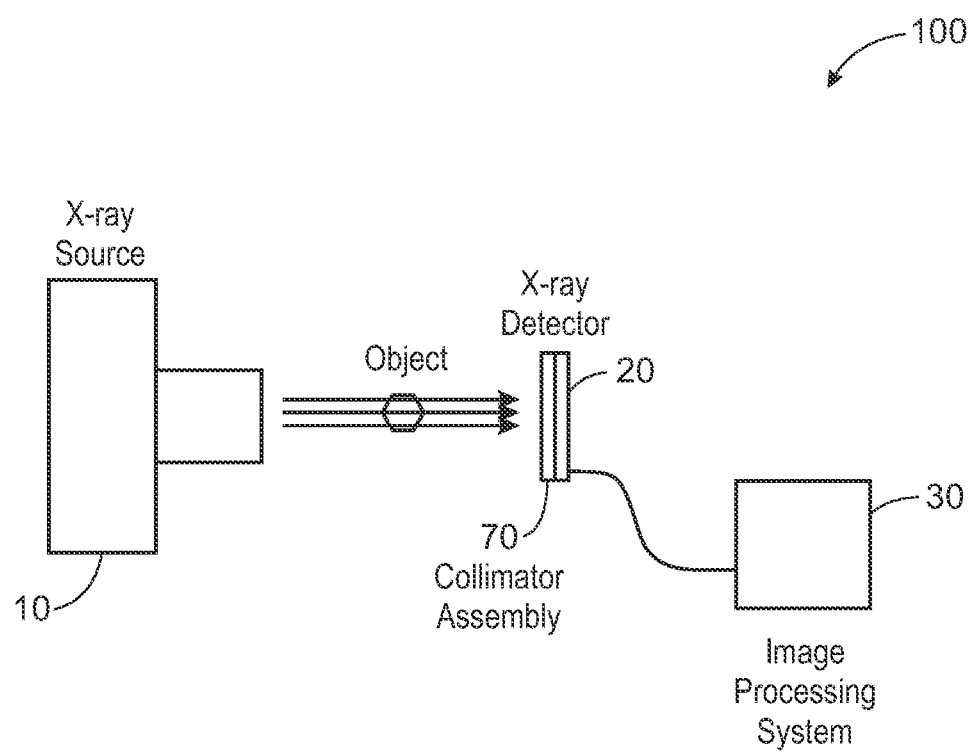
FIGS. 1A and 1B are schematic diagrams illustrating an example of an overall X-ray imaging system.
Figure 1B:
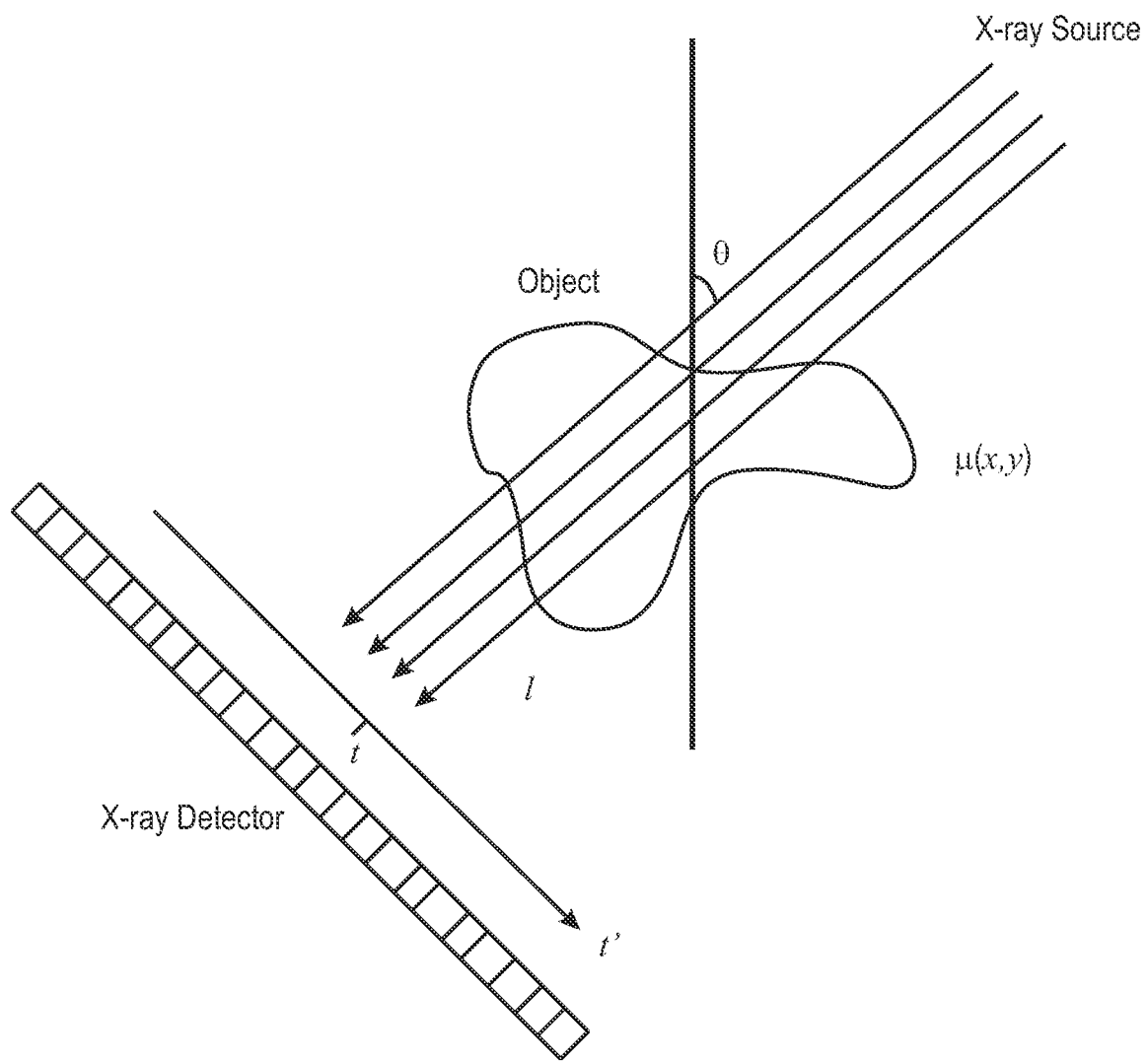

In an embodiment, the computer 50 also performs post-processing and image reconstruction of the image data output from the X-ray detector 20. The computer 50 thereby corresponds to the image processing system 30 as shown in FIGS. 1A and 2. The associated display 62 allows the operator to observe the reconstructed images and other data from the computer 50.

The X-ray source 10 arranged in the gantry 11 emits X-rays. An X-ray detector 20, which may be in the form of a photon-counting X-ray detector, detects the X-rays after they have passed through the object or patient. The X-ray detector 20 may for example be formed by plurality of pixels, also referred to as sensors or detector elements, and associated processing circuitry, such as Application Specific Integrated Circuits (ASICs), arranged in detector modules. A portion of the analog processing part may be implemented in the pixels, whereas any remaining processing part is implemented in, for instance, the ASICs. In an embodiment, the processing circuitry (ASICs) digitizes the analog signals from the pixels. The processing circuitry (ASICs) may also comprise a digital processing part, which may carry out further processing operations on the measured data, such as applying corrections, storing it temporarily, and/or filtering. During a scan to acquire X-ray projection data, the gantry and the components mounted thereon rotate about an iso-center 13.

Modern X-ray detectors normally need to convert the incident X-rays into electrons, this typically takes place through the photoelectric effect or through Compton interaction and the resulting electrons are usually creating secondary visible light until its energy is lost and this light is in turn detected by a photo-sensitive material. There are also detectors, which are based on semiconductors and in this case the electrons created by the X-ray are creating electric charge in terms of electron-hole pairs which are collected through an applied electric field.

There are detectors operating in an energy integrating mode in the sense that they provide an integrated signal from a multitude of X-rays. The output signal is proportional to the total energy deposited by the detected X-rays.

X-ray detectors with photon counting and energy resolving capabilities are becoming common for medical X-ray applications. The photon counting detectors have an advantage since in principle the energy for each X-ray can be measured which yields additional information about the composition of the object. This information can be used to increase the image quality and/or to decrease the radiation dose.

Generally, a photon-counting X-ray detector determines the energy of a photon by comparing the height of the electric pulse generated by a photon interaction in the detector material to a set of comparator voltages. These comparator voltages are also referred to as energy thresholds. Generally, the analog voltage in a comparator is set by a digital-to-analog converter (DAC). The DAC converts a digital setting sent by a controller to an analog voltage with respect to which the heights of the photon pulses can be compared.

A photon-counting detector counts the number of photons that have interacted in the detector during a measurement time. A new photon is generally identified by the fact that the height of the electric pulse exceeds the comparator voltage of at least one comparator. When a photon is identified, the event is stored by incrementing a digital counter associated with the channel.

When using several different threshold values, an energy-discriminating photon-counting detector is obtained, in which the detected photons can be sorted into energy bins corresponding to the various threshold values. Sometimes, this type of photon-counting detector is also referred to as a multi-bin detector. In general, the energy information allows for new kinds of images to be created, where new information is available and image artifacts inherent to conventional technology can be removed. In other words, for an energy-discriminating photon-counting detector, the pulse heights are compared to a number of programmable thresholds $(T_i-T_N)$ in the comparators and are classified according to pulse-height, which in turn is proportional to energy. In other words, a photon counting detector comprising more than one comparator is here referred to as a multi-bin photon counting detector. In the case of multi-bin photon counting detector, the photon counts are stored in a set of counters, typically one for each energy threshold. For example, counters can be assigned to correspond to the highest energy threshold that the photon pulse has exceeded. In another example, counters keep track of the number of times that the photon pulse cross each energy threshold.

As an example, edge-on is a special, non-limiting design for a photon-counting detector, where the X-ray sensors such as X-ray detector elements or pixels are oriented edge-on to incoming X-rays.

For example, such photon-counting detectors may have pixels in at least two directions, wherein one of the directions of the edge-on photon-counting detector has a component in the direction of the X-rays. Such an edge-on photon-counting detector is sometimes referred to as a depth-segmented photon-counting detector, having two or more depth segments of pixels in the direction of the incoming X-rays.

Alternatively, the pixels may be arranged as an array (non-depth-segmented) in a direction substantially orthogonal to the direction of the incident X-rays, and each of the pixels may be oriented edge-on to the incident X-rays. In other words, the photon-counting detector may be non-depth-segmented, while still arranged edge-on to the incoming X-rays.

By arranging the edge-on photon-counting detector edge-on, the absorption efficiency can be increased, in which case the absorption depth can be chosen to any length, and the edge-on photon-counting detector can still be fully depleted without going to very high voltages.

A conventional mechanism to detect X-ray photons through a direct semiconductor detector basically works as follows. The energy of the X-ray interactions in the detector material are converted to electron-hole pairs inside the semiconductor detector, where the number of electron-hole pairs is generally proportional to the photon energy. The electrons and holes are drifted towards the detector electrodes and backside (or vice versa). During this drift, the electrons and holes induce an electrical current in the electrode, a current which may be measured.

Figure 4:
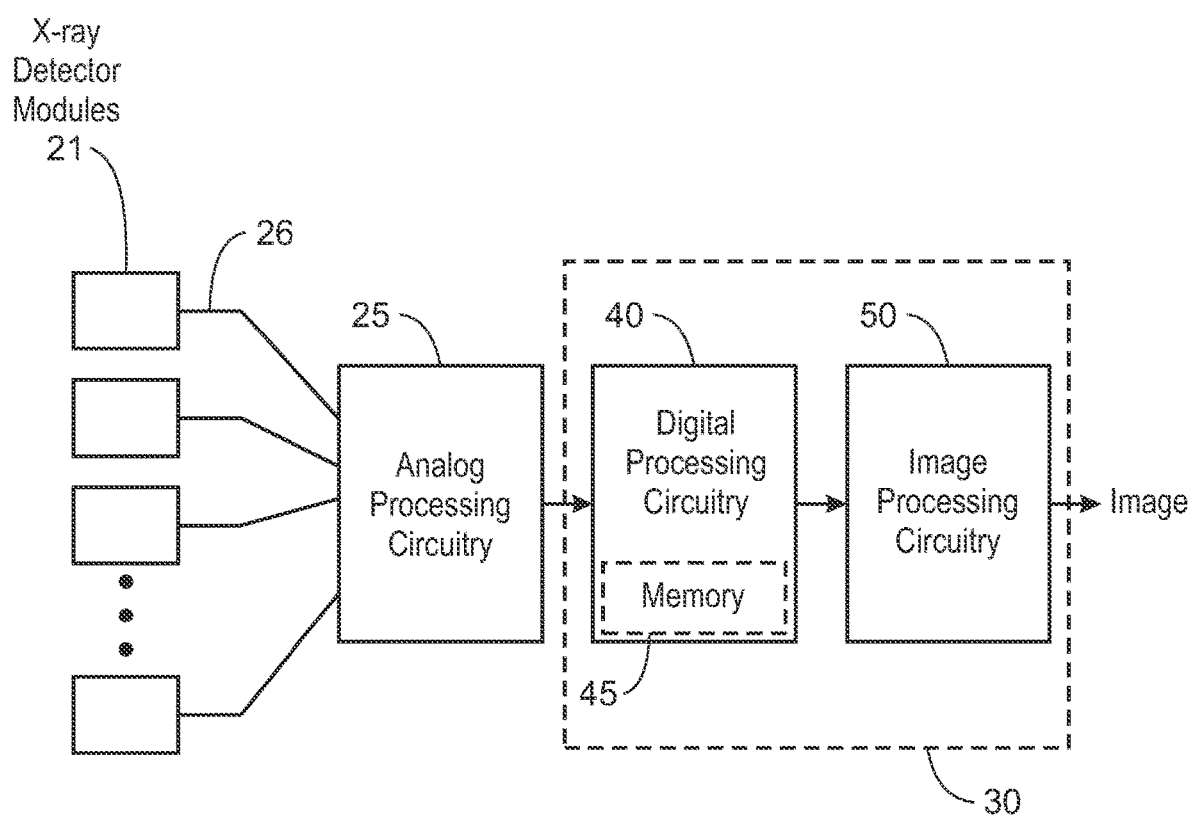
FIG. 4 is a schematic diagram illustrating another example of relevant parts of an X-ray imaging system, such as a CT imaging system.

As illustrated in FIG. 4, signal(s) 26 is/are routed from detector elements 22 of the X-ray detector to inputs of analog processing circuitry (e.g., ASICs) 25. It should be understood that the term Application Specific Integrated Circuit (ASIC) is to be interpreted broadly as any general circuit used and configured for a specific application. The ASIC processes the electric charge generated from each X-ray and converts it to digital data, which can be used to obtain measurement data such as a photon count and/or estimated energy. The ASICs are configured for connection to digital processing circuitry so the digital data may be sent to the digital processing circuitry 40 and/or one or more memory circuits or components 45 and finally the data will be the input for image processing circuitry 30 or computer 50 in FIG. 2 to generate a reconstructed image.

As the number of electrons and holes from one X-ray event is proportional to the energy of the X-ray photon, the total charge in one induced current pulse is proportional to this energy. After a filtering step in the ASIC, the pulse amplitude is proportional to the total charge in the current pulse, and therefore proportional to the X-ray energy. The pulse amplitude can then be measured by comparing its value with one or more thresholds (THR) in one or more comparators (COMP), and counters are introduced by which the number of cases when a pulse is larger than the threshold value may be recorded. In this way it is possible to count and/or record the number of X-ray photons with an energy exceeding an energy corresponding to respective threshold value (THR) which has been detected within a certain time frame.

The ASIC typically samples the analog photon pulse once every Clock Cycle and registers the output of the comparators. The comparator(s) (threshold) outputs a one or a zero depending on whether the analog signal was above or below the comparator voltage. The available information at each sample is, for example, a one or a zero for each comparator representing weather the comparator has been triggered (photon pulse was higher than the threshold) or not.

In a photon counting detector, there is typically a Photon Counting Logic which determines if a new photon has been registered and, registers the photons in counter(s). In the case of a multi-bin photon counting detector, there are typically several counters, for example one for each comparator, and the photon counts are registered in the counters in accordance with an estimate of the photon energy. The logic can be implemented in several different ways. Two of the most common categories of Photon Counting Logic are the non-paralyzable counting modes, and the paralyzable counting modes. Other photon-counting logics include, for example, local maxima detection, which counts, and possibly also registers the pulse height of, detected local maxima in the voltage pulse.

There are many benefits of photon-counting detectors including, but not limited to: high spatial resolution; less sensitivity to electronic noise; good energy resolution; and material separation capability (spectral imaging ability). However, energy integrating detectors have the advantage of high count-rate tolerance. The count-rate tolerance comes from the fact/recognition that, since the total energy of the photons is measured, adding one additional photon will always increase the output signal (within reasonable limits), regardless of the amount of photons that are currently being registered by the detector. This advantage is one of the main reasons that energy integrating detectors are the standard for medical CT today.

Figure 5:
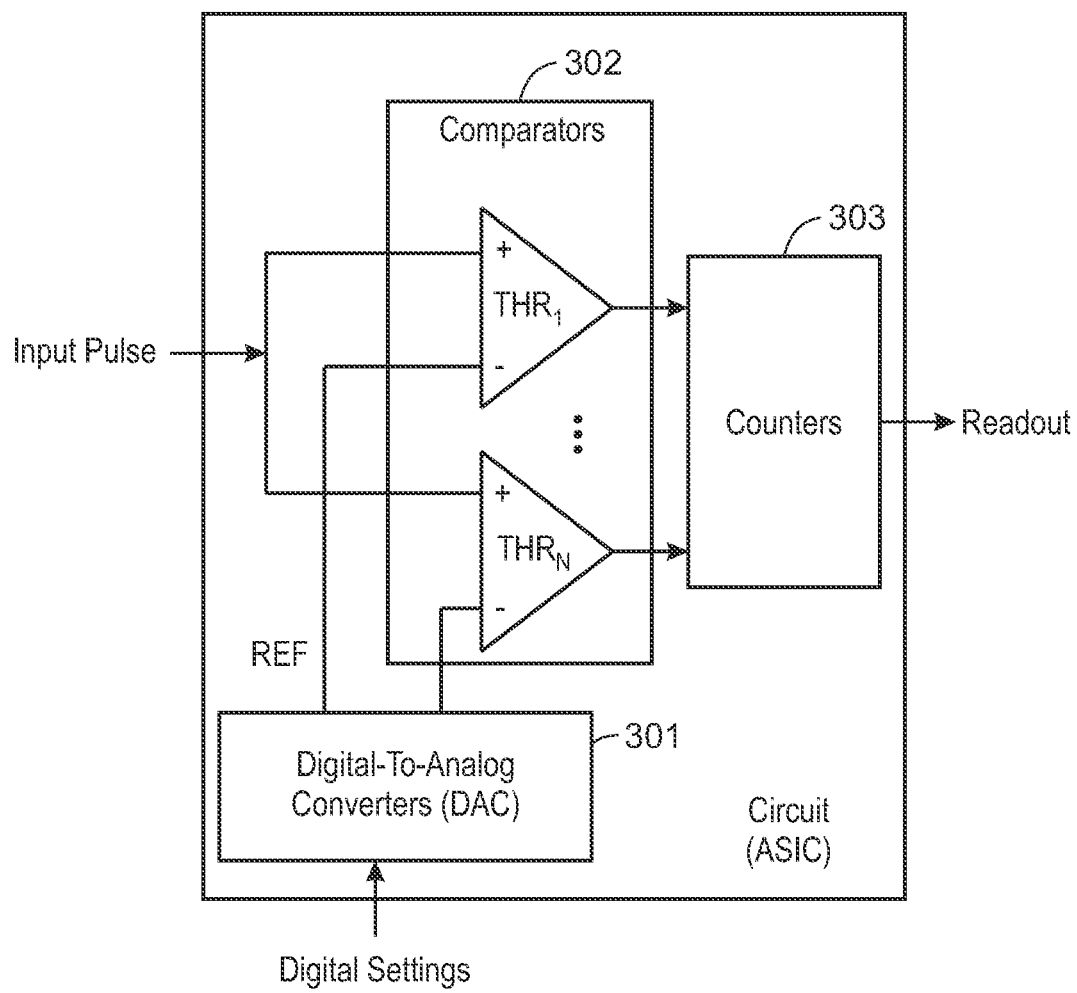
FIG. 5 is a schematic illustration of a photon-counting circuit and/or device according to prior art.

FIG. 5 shows a schematic illustration of a photon-counting circuit and/or device according to prior art.

When a photon interacts in a semiconductor material, a cloud of electron-hole pairs is created. By applying an electric field over the detector material, the charge carriers are collected by electrodes attached to the detector material. The signal is routed from the detector elements to inputs of parallel processing circuits, e.g., ASICs. It should be understood that the term Application Specific Integrated Circuit, ASIC, is to be interpreted broadly as any general circuit used and configured for a specific application. The ASIC processes the electric charge generated from each X-ray and converts it to digital data, which can be used to obtain measurement data such as a photon count and/or estimated energy. In one example, the ASIC can process the electric charge such that a voltage pulse is produced with maximum height proportional to the amount of energy deposited by the photon in the detector material.

The ASIC may include a set of comparators 302 where each comparator 302 compares the magnitude of the voltage pulse to a reference voltage. The comparator output is typically zero or one (0/1) depending on which of the two compared voltages that is larger. Here we will assume that the comparator output is one (1) if the voltage pulse is higher than the reference voltage, and zero (0) if the reference voltage is higher than the voltage pulse. Digital-to-analog converters (DACs) 301, can be used to convert digital settings, which may be supplied by the user or a control program, to reference voltages that can be used by the comparators 302. If the height of the voltage pulse exceeds the reference voltage of a specific comparator, we will refer to the comparator as triggered. Each comparator is generally associated with a digital counter 303, which is incremented based on the comparator output in accordance with the photon counting logic.

As previously mentioned, when the resulting estimated basis coefficient line integral $\hat{A}_i$ for each projection line is arranged into an image matrix, the result is a material specific projection image, also called a basis image, for each basis i. This basis image can either be viewed directly (e.g., in projection X-ray imaging) or taken as input to a reconstruction algorithm to form maps of basis coefficients $a_i$ inside the object (e.g., in CT). Anyway, the result of a basis decomposition can be regarded as one or more basis image representations, such as the basis coefficient line integrals or the basis coefficients themselves.

It will be appreciated that the mechanisms and arrangements described herein can be implemented, combined and re-arranged in a variety of ways.

For example, embodiments may be implemented in hardware, or at least partly in software for execution by suitable processing circuitry, or a combination thereof.

The steps, functions, procedures, and/or blocks described herein may be implemented in hardware using any conventional technology, such as discrete circuit or integrated circuit technology, including both general-purpose electronic circuitry and application-specific circuitry.

Alternatively, or as a complement, at least some of the steps, functions, procedures, and/or blocks described herein may be implemented in software such as a computer program for execution by suitable processing circuitry such as one or more processors or processing units.

In the following, non-limiting examples of specific detector module implementations will be discussed. More particularly, these examples refer to edge-on oriented detector modules and depth-segmented detector modules. Other types of detectors and detector modules may also be feasible.

Figure 6:
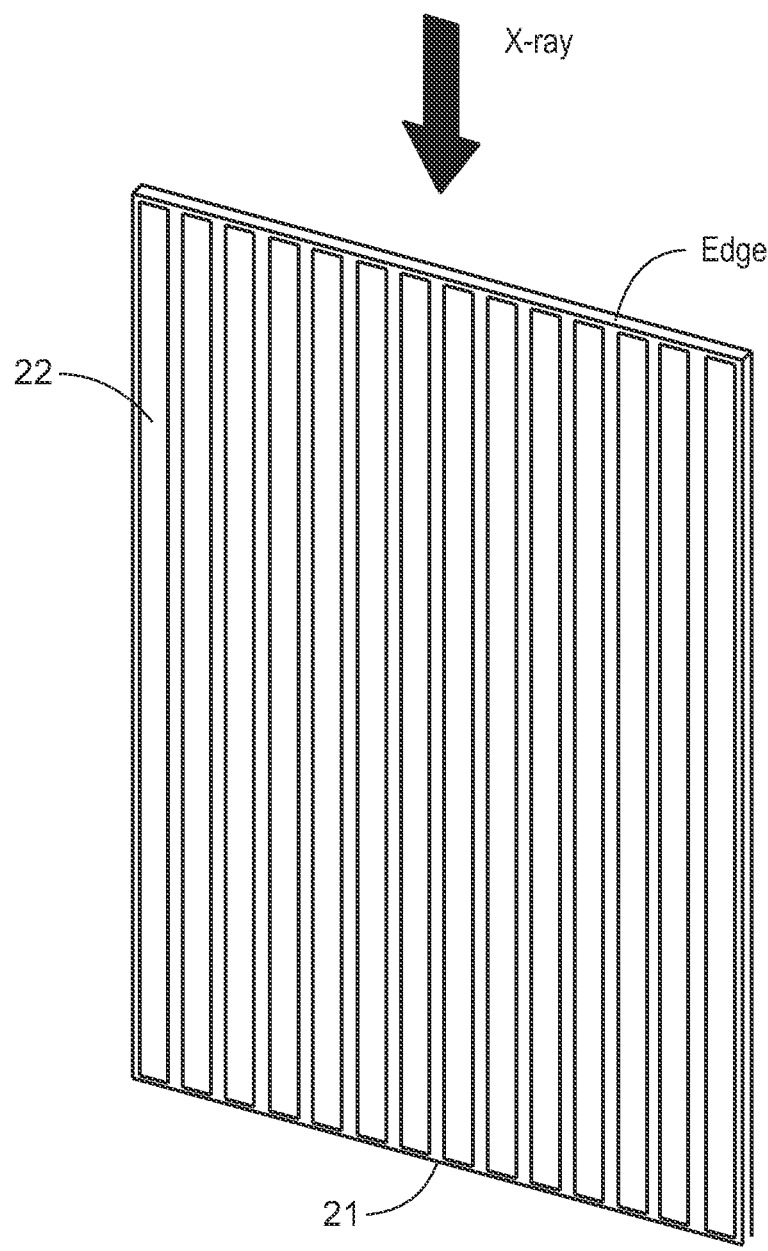
FIG. 6 is a schematic diagram illustrating an example of a semiconductor detector module according to an exemplary embodiment.

FIG. 6 is a schematic diagram illustrating an example of a semiconductor detector module according to an exemplary embodiment. This is an example of a detector module 21 with a semiconductor sensor having a plurality of detector elements or pixels 22, where each detector element (or pixel) is normally based on a diode having a charge collecting electrode as a key component. The X-rays enter through the edge of the detector module.

Figure 7:
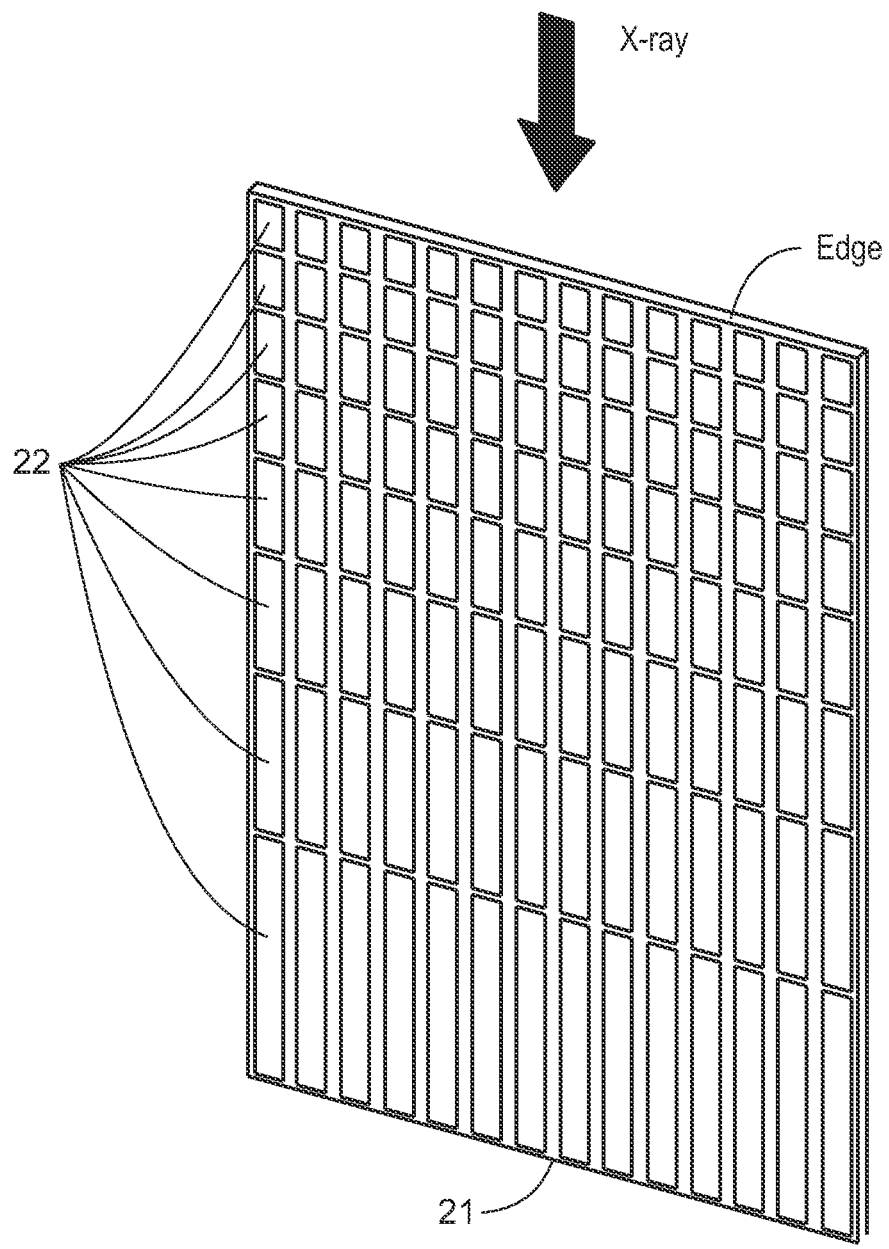
FIG. 7 is a schematic diagram illustrating an example of semiconductor detector module according to another exemplary embodiment.

FIG. 7 is a schematic diagram illustrating an example of semiconductor detector module according to another exemplary embodiment. In this example, the detector module 21 with the semiconductor sensor is also split into a plurality of depth segments or detector elements 22 in the depth direction, again assuming the X-rays enter through the edge of the detector module.

Normally, a detector element is an individual X-ray sensitive sub-element of the detector. In general, the photon interaction takes place in a detector element and the thus generated charge is collected by the corresponding electrode of the detector element.

Each detector element typically measures the incident X-ray flux as a sequence of frames. A frame is the measured data during a specified time interval, called frame time.

Depending on the detector topology, a detector element may correspond to a pixel, especially when the detector is a flat-panel detector. A depth-segmented detector may be regarded as having a number of detector strips, each strip having a number of depth segments. For such a depth-segmented detector, each depth segment may be regarded as an individual detector element, especially if each of the depth segments is associated with its own individual charge collecting electrode.

The detector strips of a depth-segmented detector normally correspond to the pixels of an ordinary flat-panel detector, and therefore sometimes also referred to as pixel strips. However, it is also possible to regard a depth-segmented detector as a three-dimensional pixel array, where each pixel (sometimes referred to as a voxel) corresponds to an individual depth segment/detector element.

The semiconductor sensors may be implemented as so called Multi-Chip Modules (MCMs) in the sense that the semiconductor sensors are used as base substrates for electric routing and for a number of ASICs which are attached preferably through so called flip-chip technique. The routing will include a connection for the signal from each pixel or detector element to the ASIC input as well as connections from the ASIC to external memory and/or digital data processing. Power to the ASICs may be provided through similar routing taking into account the increase in cross-section which is required for the large currents in these connections, but the power may also be provided through a separate connection. The ASICS may be positioned on the side of the active sensor and this means it can be protected from the incident X-rays if an absorbing cover is placed on top and it can also be protected from scattered X-rays from the side by positioning an absorber also in this direction.

Figure 8A:
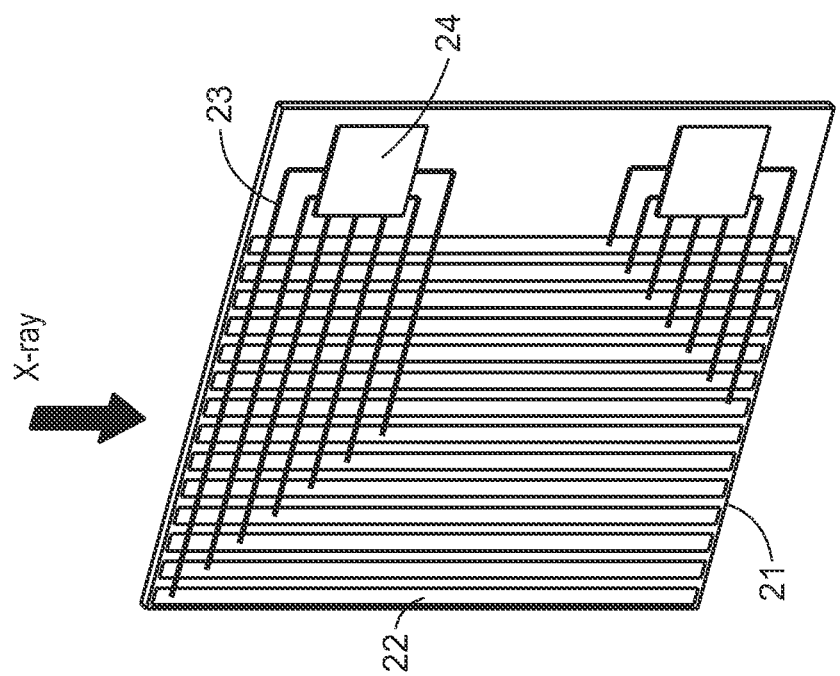
FIG. 8A is a schematic diagram illustrating an example of a semiconductor detector module according to yet another exemplary embodiment.

FIG. 8A is a schematic diagram illustrating a detector module implemented as a MCM similar to embodiments in U.S. Pat. No. 8,183,535. In this example, it is illustrated how a detector module 21 also can have the function of a substrate in a MCM. The signals are routed by routing paths 23 from the detector elements 22 to inputs of parallel processing circuits 24 (e.g., ASICs) that are positioned next to the active sensor area. It should be understood that the term Application Specific Integrated Circuit (ASIC) is to be interpreted broadly as any general integrated circuit used and configured for a specific application. The ASICs process the electric charge generated from each X-ray and converts it to digital data which can be used to detect a photon and/or estimate the energy of the photon. The ASICs may have their own digital processing circuitry and memory for small tasks. And, the ASICs may be configured for connection to digital processing circuitry and/or memory circuits or components located outside of the MCM and finally the data will be used as input for reconstructing an image.

However, the employment of depth segments also brings two noticeable challenges to a silicon-based photon-counting detector. First, a large number of ASIC channels has to be employed to process data fed from the associated detector segments. In addition to the increased number of channels due to both the smaller pixel size and the depth segmentation, multi-energy bin further increases the data size. Second, since the given X-ray input counts are divided into smaller pixels, segments and energy bins, each bin has much lower signal and so the detector calibration/correction requires more than several orders of magnitude more calibration data to minimize statistical uncertainty.

Naturally, the several orders of magnitude larger data size slow down both data handling and pre-processing in addition to the need of larger computing resources, hard drive, memory and central processing unit (CPU)/graphics processing unit (GPU). When the size of data is 10 Gigabytes instead of 10 Megabytes, for example, the data handling time, read and write, can take 1000 times longer.

A problem in any counting X-ray photon detector is the pile-up problem. When the flux rate of X-ray photons is high there may be problems in distinguishing between two subsequent charge pulses. As mentioned above, the pulse length after the filter depends on the shaping time. If this pulse length is larger than the time between two X-ray photon induced charge pulses, the pulses will grow together, and the two photons are not distinguishable and may be counted as one pulse. This is called pile-up. One way to avoid pile-up at high photon flux is thus to use a small shaping time, or to use depth-segmentation.

Figure 8B:
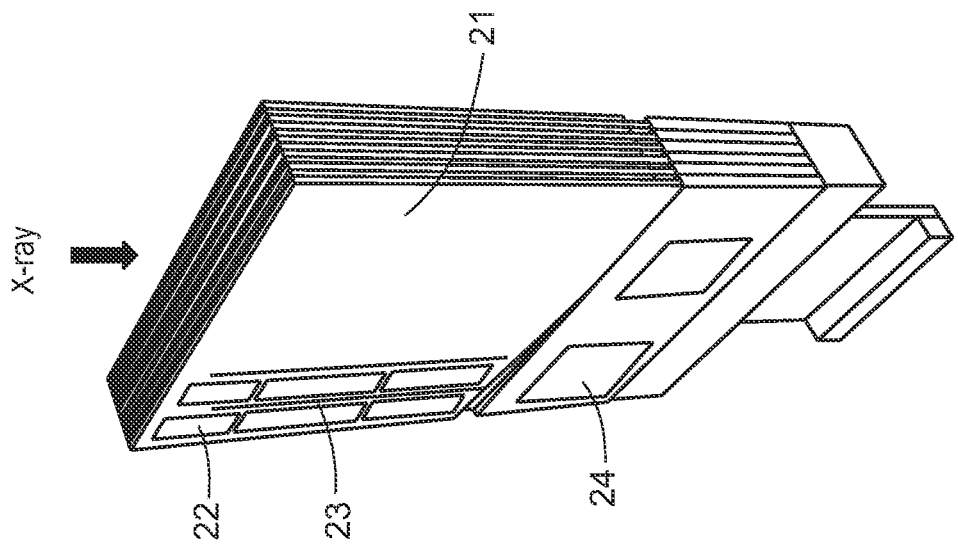
FIG. 8B is a schematic diagram illustrating an example of a set of tiled detector modules, where each detector module is a depth-segmented detector module and the Application Specific Integrated Circuits (ASICs) or corresponding circuitry are arranged below the detector elements as seen from the direction of the incoming X-rays.

FIG. 8B is a schematic diagram illustrating an example of a set of tiled detector modules, where each detector module is a depth-segmented detector module and the ASICs or corresponding circuitry 24 are arranged below the detector elements 22 as seen from the direction of the incoming X-rays, allowing for routing paths 23 from the detector elements 22 to the parallel processing circuits 24 (e.g., ASICs) in the space between detector elements.

Figure 9:
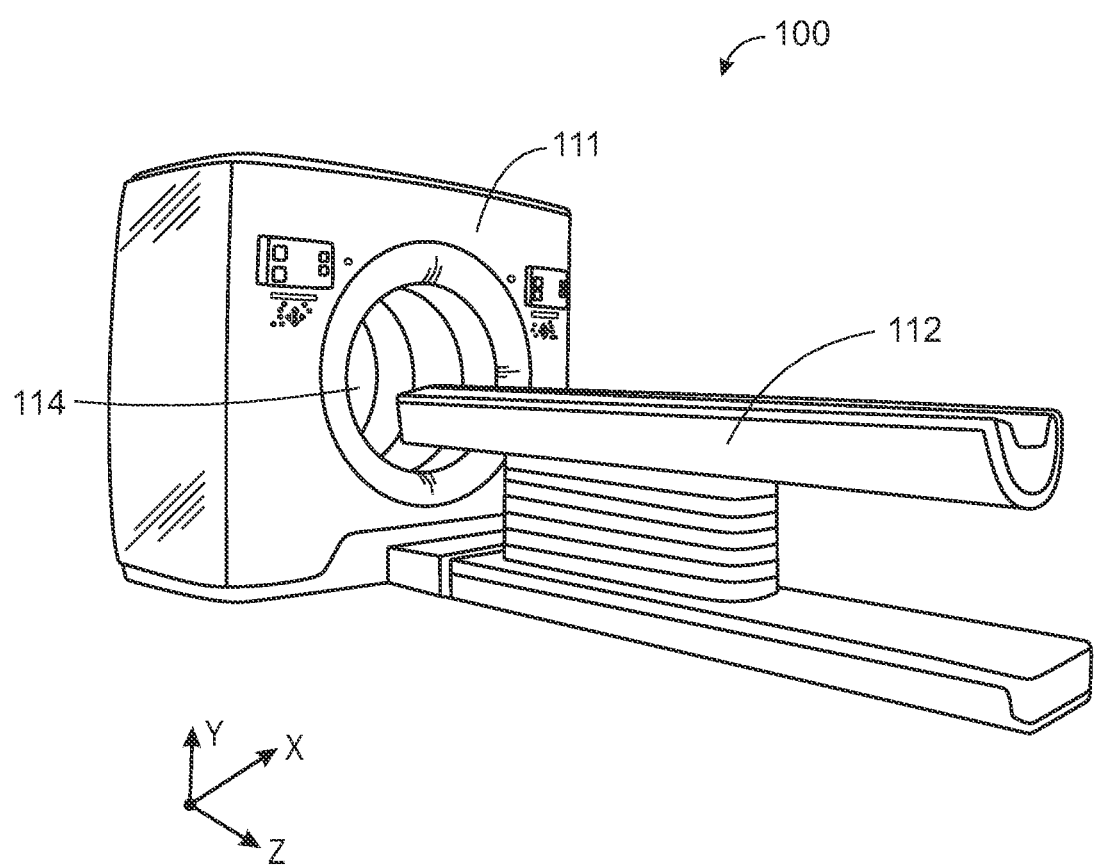
FIG. 9 is a schematic diagram illustrating an overview example of a CT imaging system.

FIG. 9 is a schematic diagram illustrating an overview example of a CT imaging system. In this schematic example, the overall CT imaging system 100 comprises a gantry 111, a patient table 112 that can be inserted into an opening 114 of the gantry 111 during a patient scan and/or a calibration scan. The direction of the rotational axis of a rotating part of the gantry around a subject or patient being imaged is denoted as the z-direction. The angular direction of the CT imaging system is denoted as the x-direction, and the direction of the incident X-rays is referred to as the y-direction.

Figure 10:
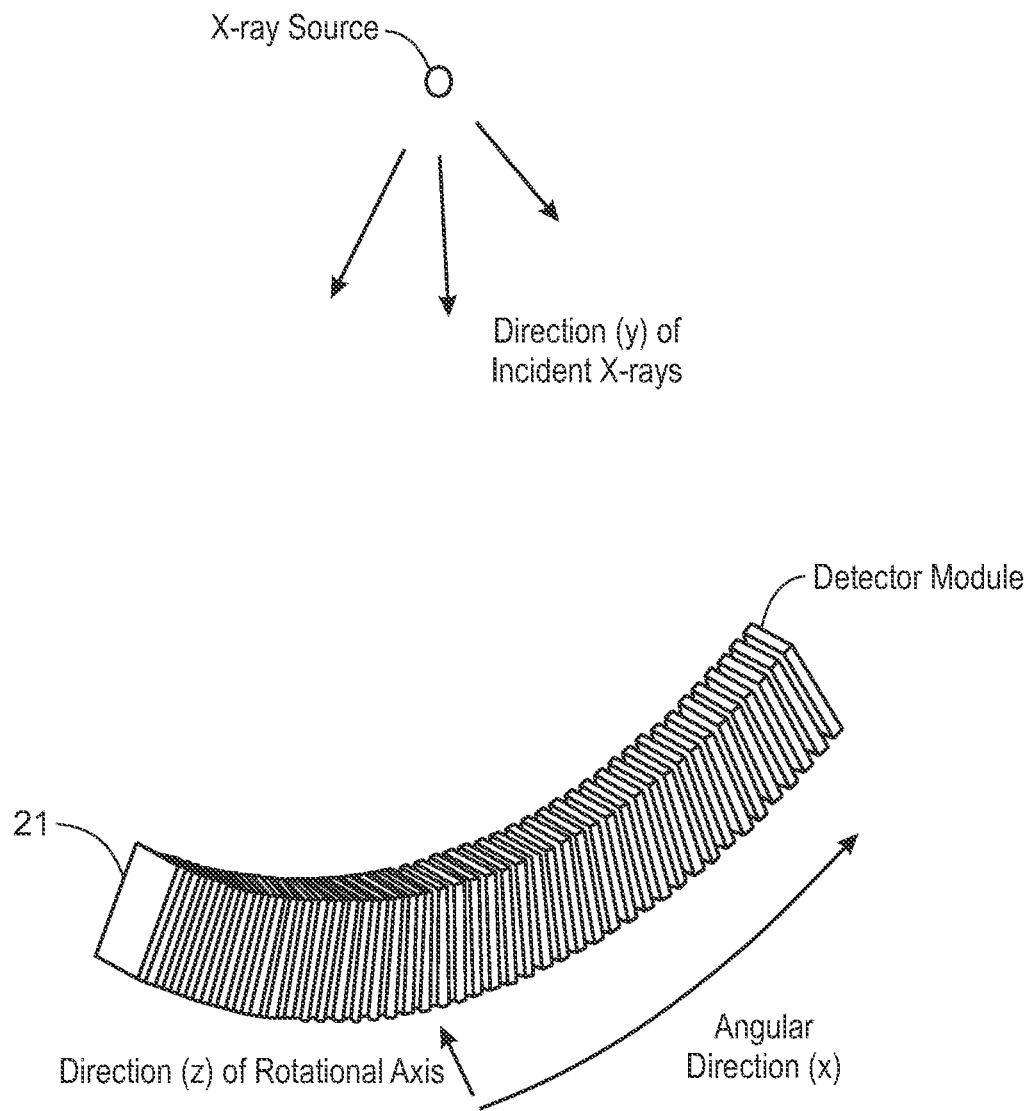
FIG. 10 is a schematic diagram illustrating an example of an overall design of an X-ray source-detector system.

FIG. 10 is a schematic diagram illustrating an example of an overall design of an X-ray source-detector system. In this example there is shown a schematic view of an X-ray detector comprising a plurality of detector modules and an X-ray source emitting X-rays. Each detector module may have a set of detector elements defining corresponding pixels. For example, the detector modules may be edge-on detector modules, arranged side-by-side and oriented edge-on pointing back to the X-ray source, and they may be arranged in a slightly curved overall configuration. As mentioned above, the direction of the incident X-rays is referred to as the y-direction. A plurality of detector pixels in the direction of the rotational axis of the gantry (referred as z-direction) enables multi-slice image acquisition. A plurality of detector pixels in the angular direction (referred as x-direction) enables measurement of multiple projections in the same plane simultaneously and this is applied in fan/cone-beam CT. The x-direction is sometimes also referred to as the channel direction. Most detectors have detector pixels in both the slice (z) direction and the angular (x) direction.

Anti-scatter or object collimators or more generally collimator assemblies, also referred to as scatter rejection grids or anti-scatter grids, are commonly used in modern CT imaging systems, e.g., to reduce the amount of object scatter in order to increase the image quality. Such a collimator assembly is normally arranged in the X-ray path between the X-ray source and the X-ray detector. When the collimator assembly is arranged "downstream" of the object or patient to be imaged, i.e., positioned between the object to be scanned and the X-ray detector, the collimator assembly is often referred to as a post-patient collimator.

The present invention relates to an X-ray imaging system comprising an X-ray source, an X-ray detector and a collimator assembly coupled to the X-ray detector. The X-ray detector comprises a plurality of detector modules arranged side-by-side and oriented towards the X-ray source, the detector modules being arranged side-by-side along a direction substantially orthogonal to the direction of incoming X-rays. The collimator assembly includes a plurality of spaced apart collimator plates arranged side-by-side in a direction coinciding with the direction of the detector modules. The collimator assembly further comprises a physically stabilizing lateral support structure arranged in a lateral plane extending in a direction substantially orthogonal to the direction of incoming X-rays.

By way of example, the X-ray imaging system may include an X-ray source, an edge-on X-ray detector and an intermediate collimator assembly in the X-ray path between the X-ray source and the X-ray detector.

In a particular example, the X-ray detector comprises a plurality of edge-on detector modules arranged side-by-side and adapted to be oriented edge-on towards the X-ray source. The detector modules are arranged side-by-side along a main extension direction substantially orthogonal to the direction of incoming X-rays.

For example, the collimator assembly may be based on a plurality of spaced collimator plates arranged side-by-side in a single direction only, coinciding with the main extension direction of the detector modules, thereby defining a one-dimensional collimator assembly composed of a solitary stack of collimator plates.

As an example, the collimator assembly further comprises a physically stabilizing lateral support structure arranged in a lateral plane extending in the main extension direction and the direction of incoming X-rays, wherein the physically stabilizing lateral support structure is attached to at least part of a short side of at least a subset of the collimator plates to improve the rigidity of the one-dimensional collimator assembly.

The collimator will be less sensitive to deformation caused by various forces occurring during operation of the X-ray imaging system, e.g., when performing a patient scan. In addition, the improvements with respect to rigidity allows the use of relatively tall collimator plates in the direction of the incoming x-rays, which in turn enables high scatter rejection. The possibility to use a one-dimensional collimator assembly makes manufacturing comparably easier than using a more complex two-dimensional collimator assembly.

By way of example, the X-ray imaging system may be a Computed Tomography (CT) imaging system, such as that illustrated in FIG. 9 and/or FIG. 10.

In a particular example, the collimator plates are arranged side-by-side in the direction of the rotational axis of the CT imaging system, also denoted as the z-direction, thereby defining a z-only collimator.

Alternatively, the collimator plates may be arranged side-by-side in the angular direction of the CT imaging system, also denoted as the x-direction, thereby defining an x-only collimator.

In a specific example, the physically stabilizing lateral support structure comprises a number of strips and/or wires extending in the lateral plane and attached to at least part of a short side of at least a subset of the collimator plates.

In another example, the physically stabilizing lateral support structure is formed as a fence and/or a grid attached to at least part of a short side of at least a subset of the collimator plates.

In yet another example, the physically stabilizing lateral support structure comprises at least one side plate having a plurality of openings therein and attached to at least part of a short side of at least a subset of the collimator plates.

By way of example, the side plate(s) having the plurality of openings therein may be a honeycomb-shaped plate.

In still another example, the physically stabilizing lateral support structure comprises at least one side cover sheet attached to at least part of a short side of at least a subset of the collimator plates.

Optionally, the physically stabilizing lateral support structure may be arranged on both sides of the collimator plates.

For example, the physically stabilizing lateral support structure may include or be made of Carbon Fiber Reinforced Polymers (CFRP). In fact, experimental studies have shown that the use of CFRP as a base material for the physically stabilizing lateral support structure makes it possible to significantly reduce the maximum deformation of the collimator during operation in a rotating CT imaging system.

In a particular example, the collimator assembly further comprises a top holding plate and a bottom holding plate to which the collimator plates are attached.

By way of example, the top holding plate and the bottom holding plate may be carbon caps.

Optionally, the collimator assembly further comprises a hardened foam layer provided between at least a subset of the collimator plates. For example, ROHACELL® may be used as the core material for the foam layer.

In a specific example, at least a subset of the collimator plates may be arranged for alignment with spaces or gaps defined between adjacent detector modules.

Optionally, an X-ray attenuating assembly may be arranged between at least a subset of the detector modules. In a practical example, at least one of the collimator plates may be provided as an extension of the X-ray attenuating assembly.

By way of example, the X-ray attenuating assembly may comprise at least one X-ray attenuating plate or sheet or anti-scatter foil.

In a particular example, each detector module has an array of detector elements extending in the direction of incoming X-rays and a direction orthogonal to both the direction of incoming X-rays and the main extension direction, and each of the collimator plates extends in the same directions.

Optionally, the physically stabilizing lateral support structure is attached to at least part of a short side of at least a subset of the collimator plates by an adhesive such as epoxy, glue or potting.

For a better understanding, the proposed technology will now be described in further detail with reference to the non-limiting examples of FIGS. 12-23.

Figure 11A:
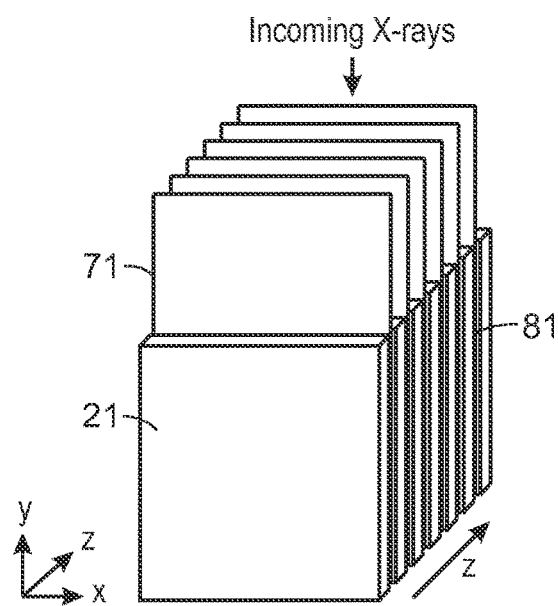
FIG. 11A is a schematic diagram illustrating an example of a detector-collimator assembly having a one-dimensional collimator assembly composed of a plurality of collimator plates arranged side-by-side in the direction of the rotational axis of a CT imaging system, also denoted as the z-direction, thereby defining a z-only collimator.

FIG. 11A is a schematic diagram illustrating an example of a detector-collimator assembly having a one-dimensional collimator assembly composed of a plurality of collimator plates arranged side-by-side in the direction of the rotational axis of a CT imaging system, also denoted as the z-direction, thereby defining a z-only collimator.

As can be seen, there's a plurality of edge-on detector modules 21 arranged side-by-side and adapted to be oriented edge-on towards the X-ray source. The detector modules 21 are arranged side-by-side along a main extension direction (z) substantially orthogonal to the direction (y) of incoming X-rays.

The collimator assembly is based on a plurality of spaced collimator plates 71 arranged side-by-side in a single direction only, coinciding with the main extension direction (z) of the detector modules, thereby defining a one-dimensional collimator assembly composed of a solitary stack of collimator plates.

In this particular example, the collimator plates are arranged side-by-side in the direction (z) of the rotational axis of a CT imaging system, to form a z-only collimator.

By way of example, the collimator plates 71 may comprise a high Z material, such as tungsten.

In a particular example, an X-ray attenuating assembly 81 may be arranged between at least a subset of the edge-on detector modules 21. By way of example, the X-ray attenuating assembly 81 may comprise at least one X-ray attenuating plate or sheet or anti-scatter foil. In other words, for at least a subset of the detector modules, adjacent edge-on detector modules 21 may have an optional anti-scatter foil, sheet or plate 81 located in the gap between the detector modules 21. This optional feature may provide additional anti-scatter protection and/or reduction of detector cross-talk. The anti-scatter foil, sheet or plate may, just like the collimator plates, in a particular embodiment comprise a high Z material, such as tungsten.

Figure 11B:
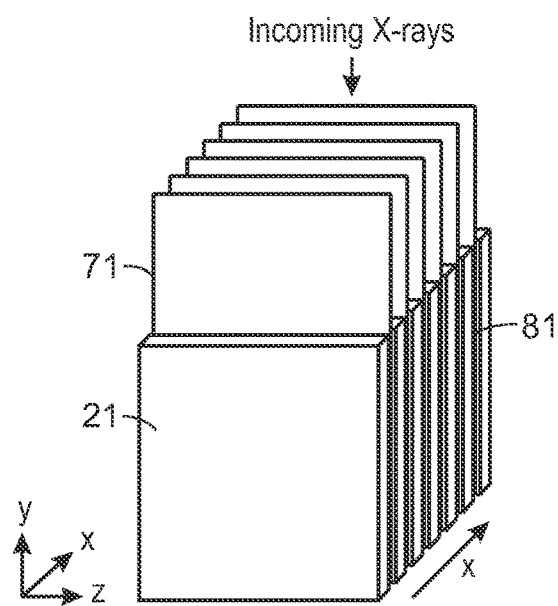
FIG. 11B is a schematic diagram illustrating an example of a detector-collimator assembly having a one-dimensional collimator assembly composed of a plurality of collimator plates arranged side-by-side in the angular direction of a CT imaging system, also denoted as the x-direction, thereby defining an x-only collimator.

FIG. 11B is a schematic diagram illustrating an example of a detector-collimator assembly having a one-dimensional collimator assembly composed of a plurality of collimator plates arranged side-by-side in the angular direction of a CT imaging system, also denoted as the x-direction, thereby defining an x-only collimator.

When comparing z-only collimators and x-only collimators, the inventors have realized that z-only collimators may be less sensitive to the rotational forces in a CT imaging system, with respect to deformation.

Figure 12:
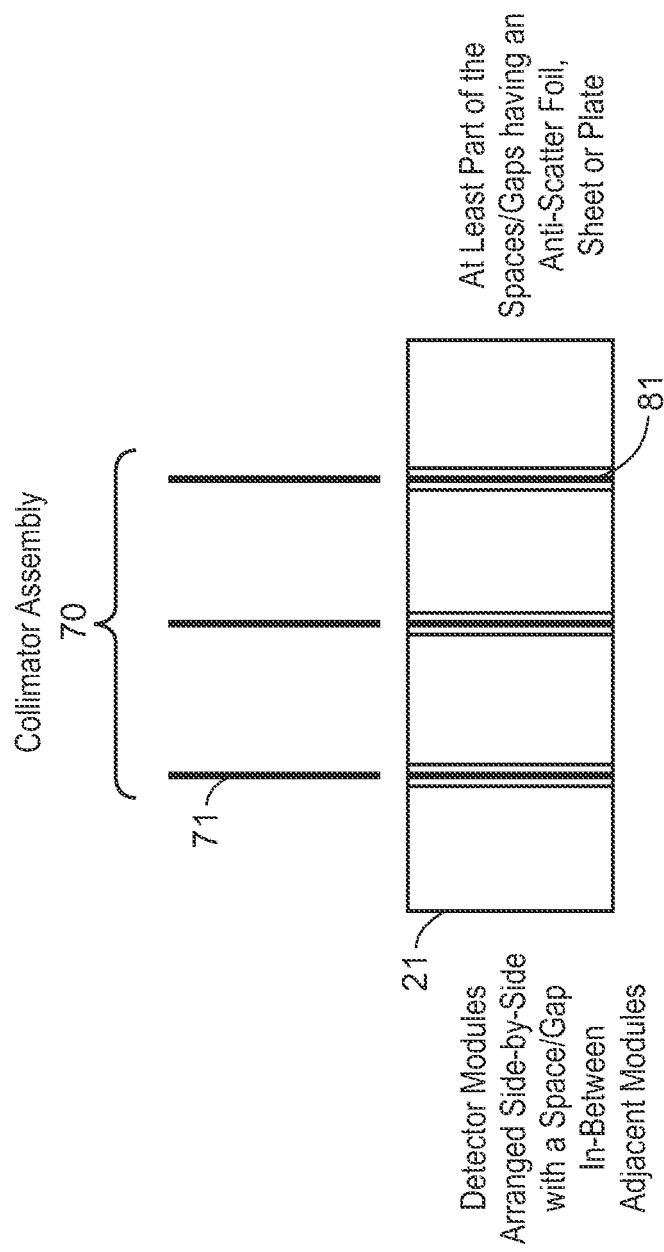
FIG. 12 is a schematic cross-section diagram illustrating an example of a detector-collimator assembly according to an embodiment.

FIG. 12 is a schematic cross-section diagram illustrating an example of a detector-collimator assembly according to an embodiment. In this example, the detector modules 21 are arranged side-by-side with spaces/gaps defined in-between the modules, wherein the spaces/gaps are provided with an anti-scatter foil, sheet or plate 81 that may be fastened or otherwise attached to the detector modules 21. Here, the collimator plates 71, which define the overall one-dimensional collimator assembly 70, are aligned with the anti-scatter foils, sheets or plates 81. By positioning the collimator plates in alignment with and/or on top of inactive (dead/gap) regions of the overall detector, the detection efficiency is improved.

Figure 13:
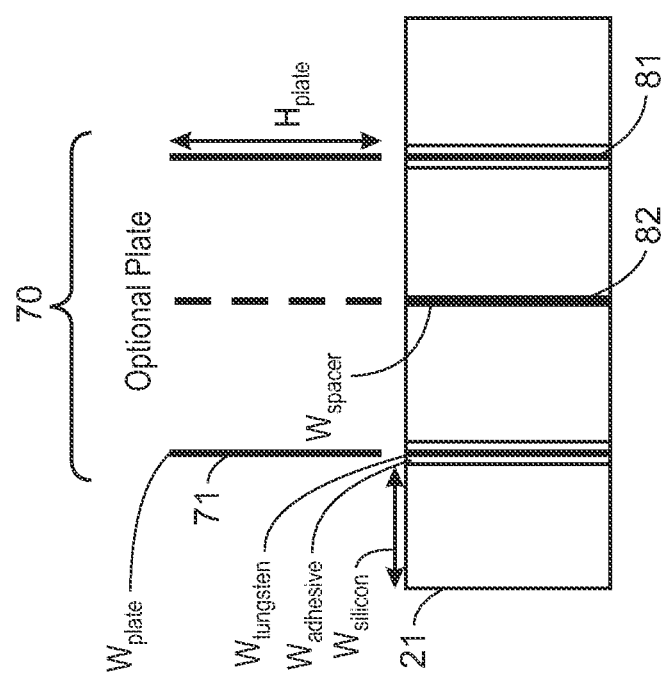
FIG. 13 is a schematic cross-section diagram illustrating another example of a detector-collimator assembly according to an embodiment.

FIG. 13 is a schematic cross-section diagram illustrating another example of a detector-collimator assembly according to an embodiment. In this example, not all spaces/gaps between adjacent detector modules have an anti-scatter foil, sheet or plate 81.

For example, this may be the case, if the detector modules are arranged pairwise, e.g., frontside-to-frontside. Preferably, an anti-scatter foil, sheet or plate 81 may be arranged in the frontside-to-frontside space between adjacent detector modules 21, assuming the front-end electronics of the detector modules reside on the frontside. However, it may not be necessary to provide any anti-scatter assembly in the backside-to-backside space between adjacent detector modules. It may be sufficient to only provide a spacer 82 in the backside-to-backside space between adjacent detector modules 21. These spacers 82 may be three-dimensionally (3D)-printed.

As can be seen from FIG. 13, it is also not necessary to provide a collimator plate above each gap/space between adjacent detector modules. For example, provisioning of a collimator plate above the spacer 82 is merely optional.

Figure 14:
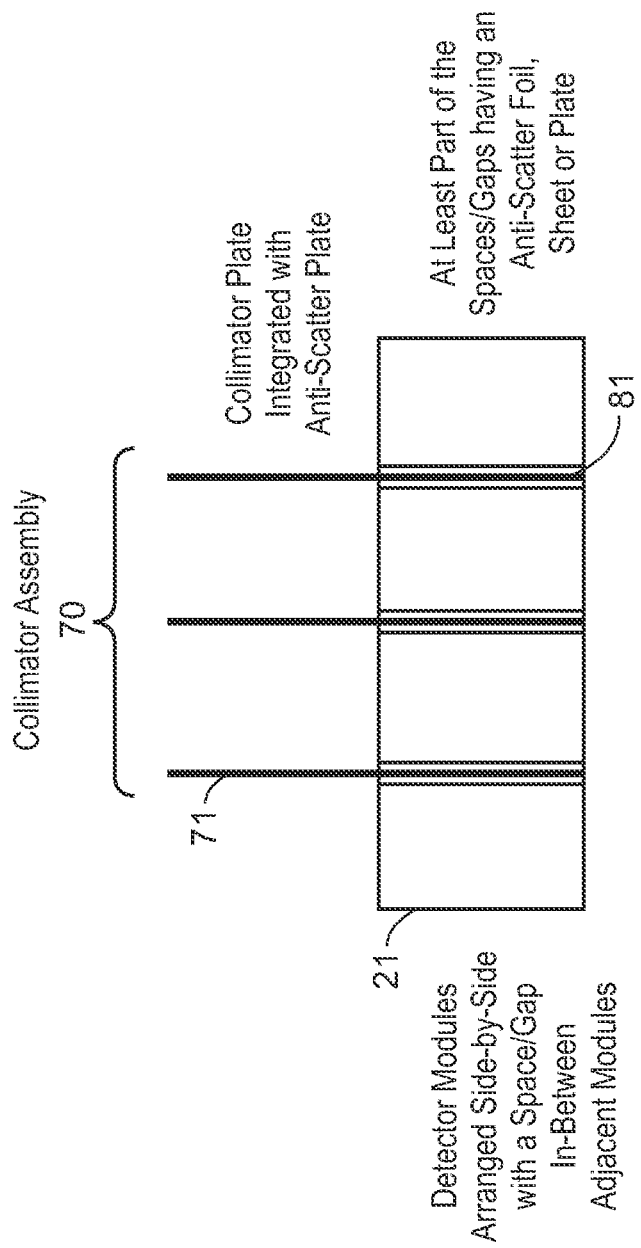
FIG. 14 is a schematic cross-section diagram illustrating yet another example of a detector-collimator assembly according to an embodiment.

FIG. 14 is a schematic cross-section diagram illustrating yet another example of a detector-collimator assembly according to an embodiment.

In this particular example, at least one of the collimator plates is provided as an extension of the X-ray attenuating assembly. More specifically, a practical solution is to integrate each collimator plate 71 with a corresponding anti-scatter foil, sheet or plate 81.

In other words, the post-patient collimator 70 may be separately attached onto the X-ray detector or integrated with the X-ray detector. The purpose of the collimator 70 is to reject object scatter that is detrimental to image quality. However, the collimator plates 71 block a fraction of primary x-rays, thereby reducing the detection efficiency. Certain embodiments of the invention alleviate this problem by directly integrating the post-patient collimator as an integral part of the detector. This invention applies particularly well to certain type of detectors, e.g., where the individual detector modules/slices (channels) are separate physical units, and/or for edge-on detector modules such as deep silicon-based edge illuminated detector modules.

In edge illuminated detectors there are normally internal plates between the detector modules/slices, primarily to suppress the internal scatter. As mentioned, according to a specific embodiment, e.g., as illustrated in FIG. 14, these internal plates extend further out to form the post-patient collimator. There are several benefits with this approach: 1)

the external part of the plates are directly located over the pre-existing spaces/gaps between detector modules/slices, and therefore does not further reduce geometric efficiency, and 2) the external part of the plates are self-aligned to the detector cells.

Figure 15:
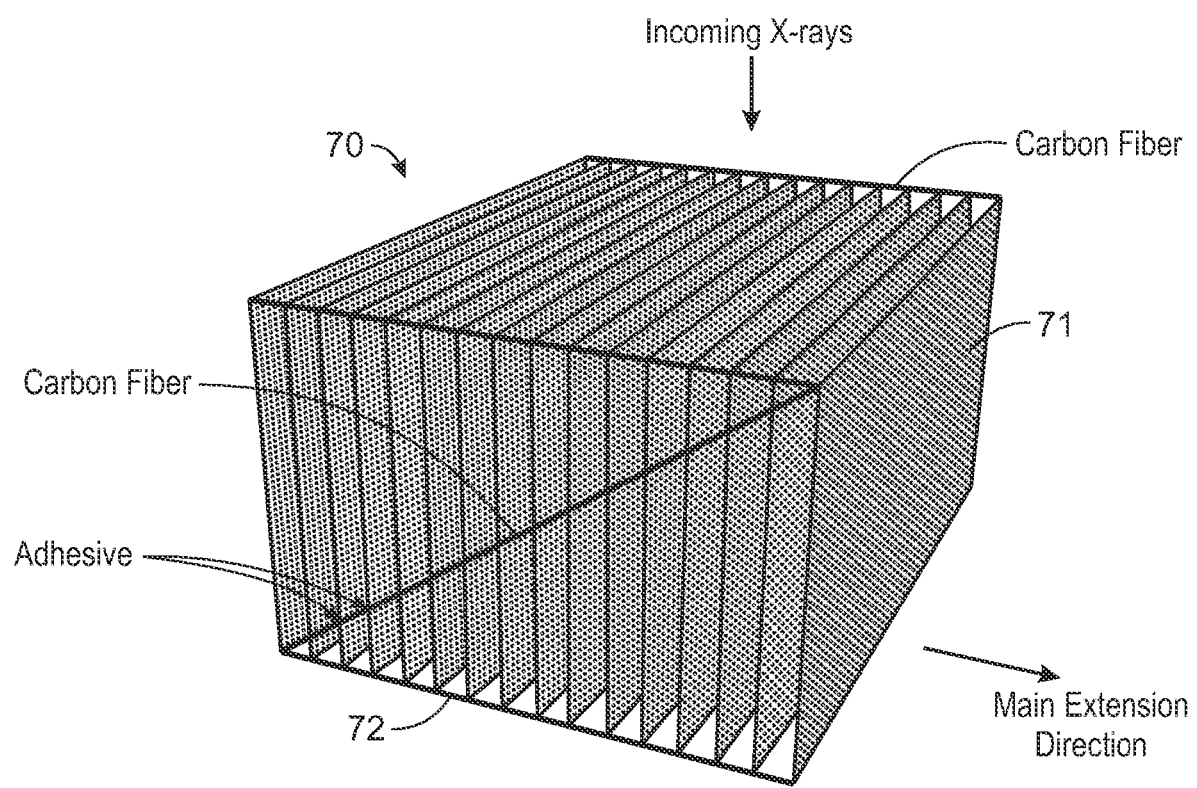
FIG. 15 is a schematic perspective diagram illustrating an example of a one-dimensional collimator assembly having a physically stabilizing lateral support structure to improve the rigidity of the one-dimensional collimator assembly.

FIG. 15 is a schematic perspective diagram illustrating an example of a one-dimensional collimator assembly 70 having a physically stabilizing lateral support structure 72 to improve the rigidity of the one-dimensional collimator assembly.

In this particular example, the physically stabilizing lateral support structure 72 comprises a number of strips and/or wires that are i) extending in the lateral plane defined by the main extension direction and the direction of incoming X-rays and ii) attached to at least part of a short side of at least a subset of the collimator plates 71. By way of example, the strips and/or wires may be made of carbon fiber, that are attached, e.g., by an adhesive such as epoxy, glue or potting, to each of the collimator plates 71 or a subset thereof at selected contact points.

It should be understood that any of wide variety of stabilizing lateral support structures may be employed, as will be exemplified below.

Figure 16:
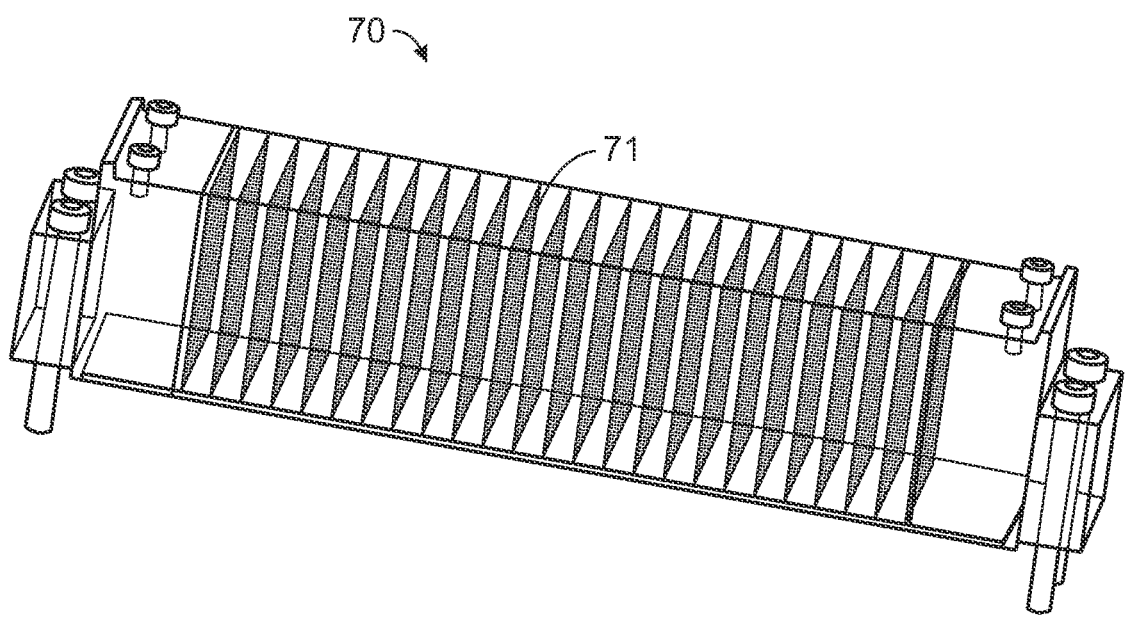
FIG. 16 is a schematic perspective diagram illustrating an example of a practical implementation a one-dimensional collimator assembly.

FIG. 16 is a schematic perspective diagram illustrating an example of a practical implementation a one-dimensional collimator assembly.

Figure 17:
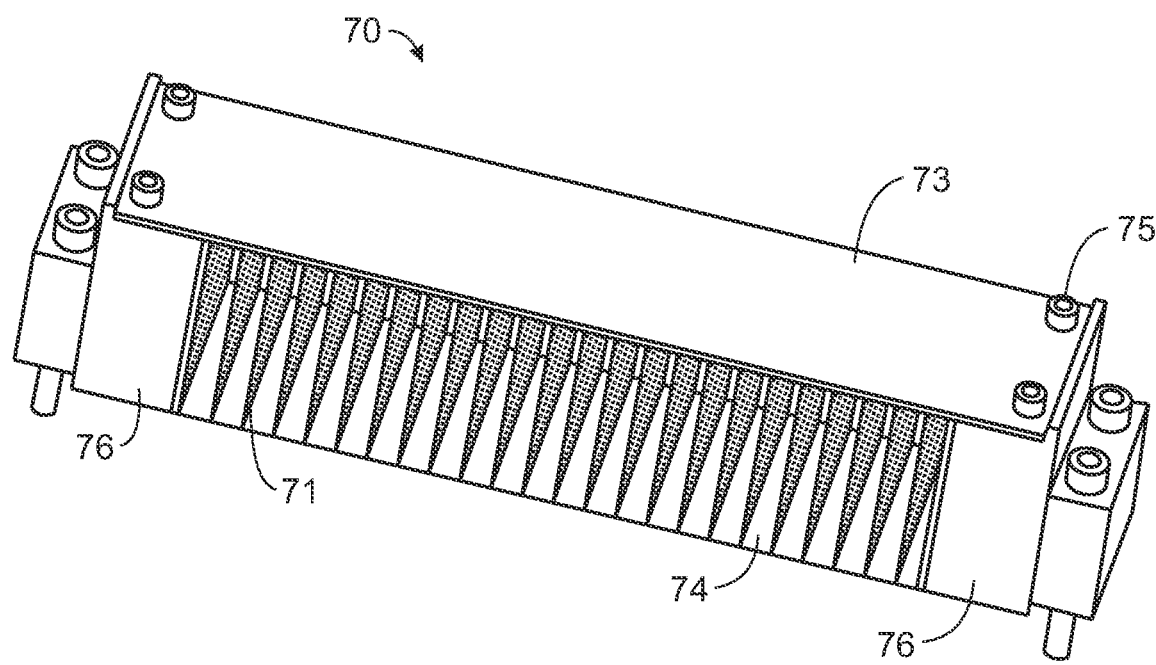
FIG. 17 is a schematic perspective diagram illustrating a particular example of a practical implementation a one-dimensional collimator assembly having holding plates to which the collimator plates are attached.

FIG. 17 is a schematic perspective diagram illustrating a particular example of a practical implementation a one-dimensional collimator assembly 70 having holding plates 73; 74 to which the collimator plates 71 are attached.

By way of example, these holding plates 73; 74 may be fastened with fasteners 75 to respective end blocks 76 of the overall collimator. In addition, the end blocks 76 may have positioning pins to which positioning holes in the holding plates 73; 74 may be aligned.

For example, this particular design may use two carbon caps as the upper and lower connecting surfaces (holding plates 73; 74) of the overall collimator 70.

The inventors have realized that this practical implementation of a collimator may still be sensitive to deformation caused by, e.g., rotational and other forces occurring during operation of an X-ray imaging system such as a CT imaging system. For example, the center part of the holding plates 73; 74 is not fixed, so the vibration generated by high-speed rotation may cause the center part of the plate to shift.

The proposed stabilizing lateral support structure that is arranged in a lateral plane extending in the main extension direction and the direction of incoming X-rays and attached to at least part of a short side of at least a subset of the collimator plates may substantially improve the rigidity of the one-dimensional collimator assembly.

Figure 18B:
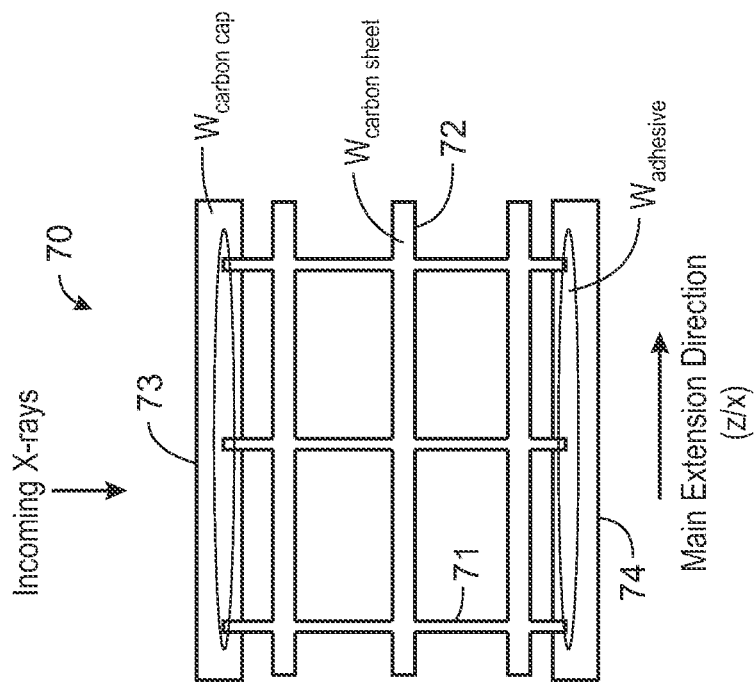
FIG. 18B is a schematic diagram illustrating a cross-section of part of the collimator assembly of FIG. 18A.
Figure 18A:
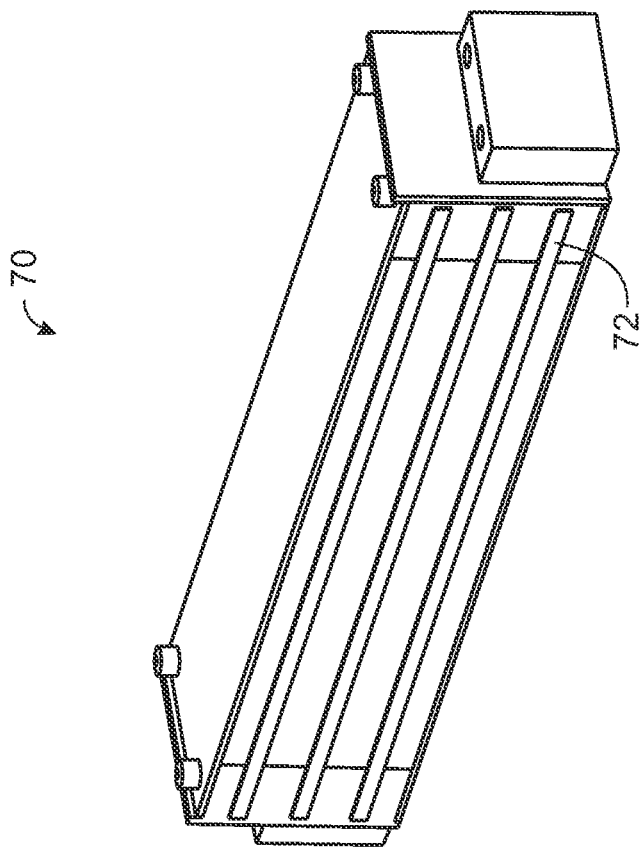
FIG. 18A is a schematic perspective diagram illustrating another example of a one-dimensional collimator assembly having a physically stabilizing lateral support structure to improve the rigidity of the one-dimensional collimator assembly.

FIG. 18A is a schematic perspective diagram illustrating another example of a one-dimensional collimator assembly 70 having a physically stabilizing lateral support structure 72 to improve the rigidity of the one-dimensional collimator assembly.

FIG. 18B is a schematic diagram illustrating a cross-section of part of the collimator assembly of FIG. 18A.

As mentioned, the physically stabilizing lateral support structure 72 may comprise a number of strips extending in the above-defined lateral plane and being attached to at least part of a short side of all or at least a subset of the collimator plates 71. In this particular example, the lateral support structure 72 is formed as a set of elongated strips or sheets extending in the main extension direction (z/x) from one end block to the other end block of the overall collimator assembly 70. By way of example, the strips may be carbon-based strips, e.g., made of CFRP. As an example, the thickness of the strips may be equal to or larger than 0.1 mm, and preferably equal to or larger than 0.3 mm.

By way of example, fixed carbon fiber strips are preferably provided on both short sides to improve the overall stiffness.

A small portion of the X-ray dose may be lost because of the added strips of the lateral support structure.

Figure 19B:
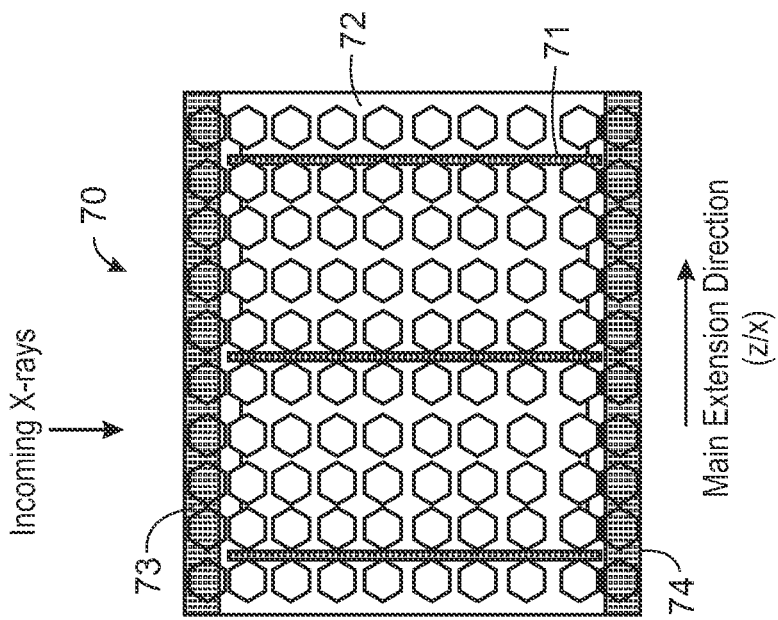
FIG. 19B is a schematic diagram illustrating a cross-section of part of the collimator assembly of FIG. 19A.
Figure 19A:
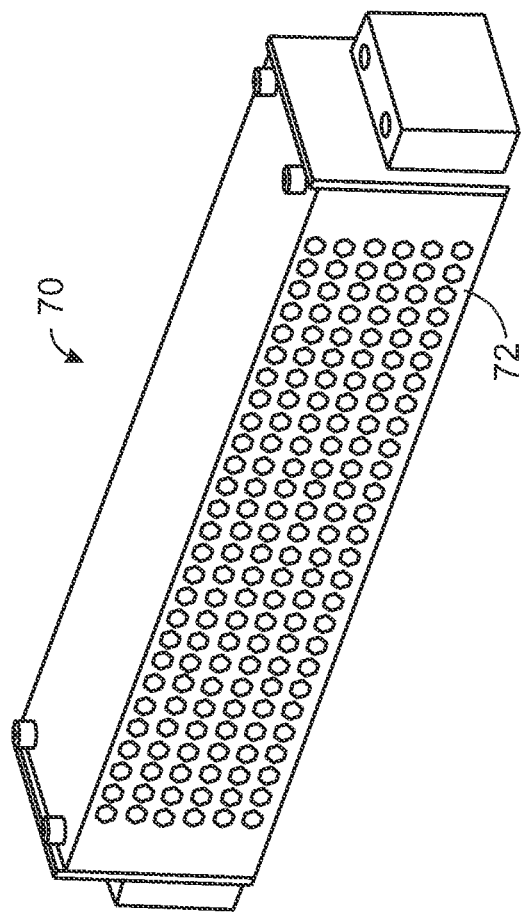
FIG. 19A is a schematic perspective diagram illustrating yet another example of a one-dimensional collimator assembly having a physically stabilizing lateral support structure to improve the rigidity of the one-dimensional collimator assembly.

FIG. 19A is a schematic perspective diagram illustrating yet another example of a one-dimensional collimator assembly 70 having a physically stabilizing lateral support structure 72 to improve the rigidity of the one-dimensional collimator assembly.

FIG. 19B is a schematic diagram illustrating a cross-section of part of the collimator assembly 70 of FIG. 19A.

In this example, the physically stabilizing lateral support structure 72 comprises at least one side plate or side cap having a plurality of openings defined therein and being attached to at least part of a short side of at least a subset of the collimator plates 71.

Preferably, the size and distribution of the openings defined in the side plate(s) are adapted to provide a balance or trade-off between stiffness and loss of X-ray dose. Overall stiffness is improved when relatively large areas of the fixed side plates are attached to the short sides of the collimator plates. On the other hand, more material in the side plate will result in higher loss of X-ray dose. The provisioning of a plurality of openings in a side plate caters for improved stiffness as well as reduced loss of X-ray dose. Preferably, the side plate(s) may, e.g., include or be made of CFRP. As an example, the thickness of the side plates or side caps may be equal to or larger than 0.1 mm, and preferably equal to or larger than 0.3 mm.

Figure 20:
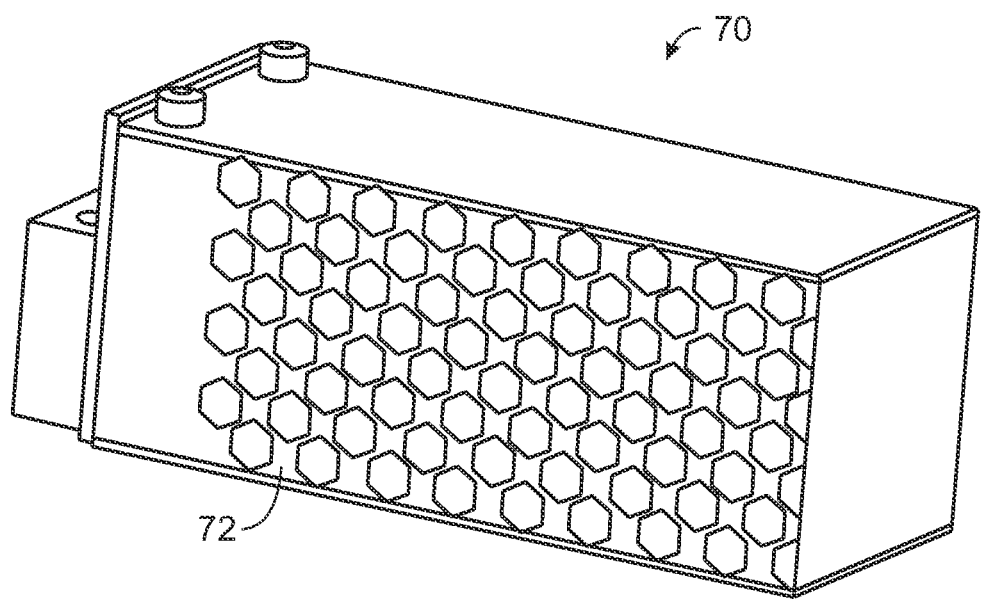
FIG. 20 is a schematic perspective diagram illustrating still another example of a one-dimensional collimator assembly having a physically stabilizing lateral support structure to improve the rigidity of the one-dimensional collimator assembly.

By way of example, the side plate(s) having openings defined therein may be a honeycomb-shaped plate, e.g., as specifically illustrated in FIG. 20.

Figure 21:
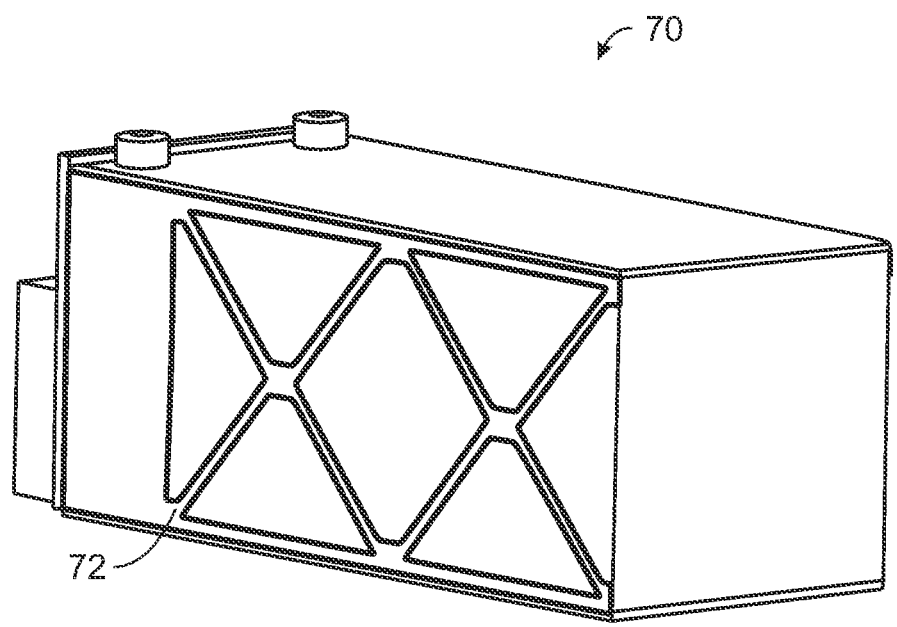
FIG. 21 is a schematic perspective diagram illustrating a further example of a one-dimensional collimator assembly having a physically stabilizing lateral support structure to improve the rigidity of the one-dimensional collimator assembly.

FIG. 21 is a schematic perspective diagram illustrating a further example of a one-dimensional collimator assembly having a physically stabilizing lateral support structure to improve the rigidity of the one-dimensional collimator assembly.

In this particular example, the physically stabilizing lateral support structure 72 is formed as a fence and/or a grid being attached to at least part of a short side of at least a subset of the collimator plates 71.

Figure 22:
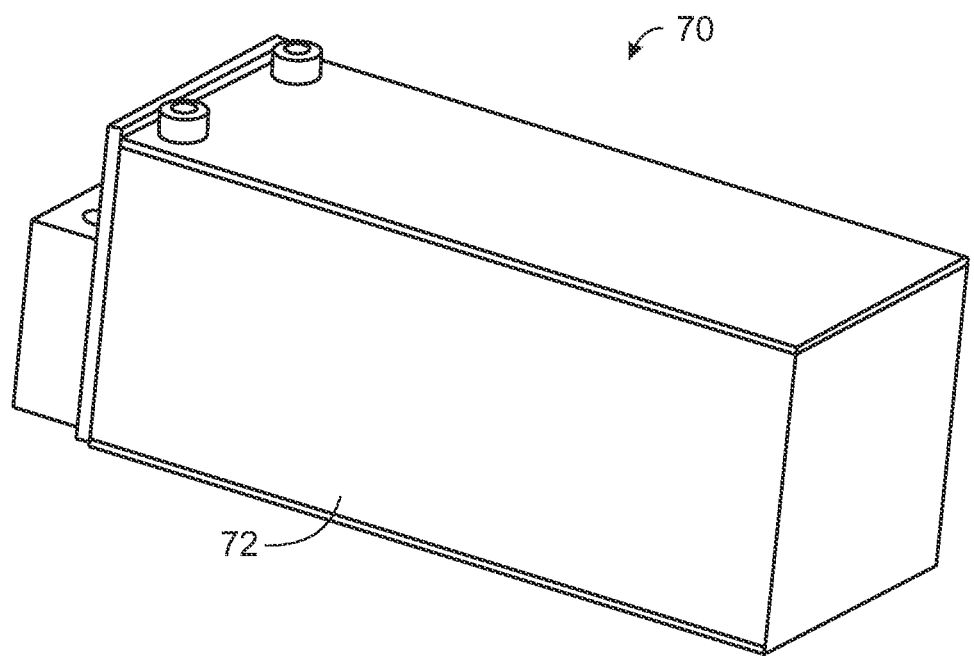
FIG. 22 is a schematic perspective diagram illustrating another further example of a one-dimensional collimator assembly having a physically stabilizing lateral support structure to improve the rigidity of the one-dimensional collimator assembly.

FIG. 22 is a schematic perspective diagram illustrating another further example of a one-dimensional collimator assembly having a physically stabilizing lateral support structure to improve the rigidity of the one-dimensional collimator assembly.

In this example, the physically stabilizing lateral support structure 72 comprises at least one side cover sheet attached to at least part of a short side of at least a subset of the collimator plates. When using two complete side caps, e.g., made of CFRP, and with an exemplifying thickness of more than 0.1 mm, the overall rigidity or stiffness shows a very good state. However, the complete side caps imply a larger loss of X-ray dose, compared to the other embodiments.

Embodiments of the present disclosure shown in the drawings and described above are example embodiments only and are not intended to limit the scope of the appended claims, including any equivalents as included within the scope of the claims. It will be understood by those skilled in the art that various modifications, combinations, and changes may be made to the embodiments without departing from the present scope as defined by the appended claims. It is intended that any combination of non-mutually exclusive features described herein are within the scope of the present invention. That is, features of the described embodiments can be combined with any appropriate aspect described above and optional features of any one aspect can be combined with any other appropriate aspect. Similarly, features set forth in dependent claims can be combined with non-mutually exclusive features of other dependent claims, particularly where the dependent claims depend on the same independent claim. Single claim dependencies may have been used as practice in some jurisdictions require them, but this should not be taken to mean that the features in the dependent claims are mutually exclusive.

It is further noted that the inventive concepts relate to all possible combinations of features unless explicitly stated otherwise. In particular, different part solutions in the different embodiments can be combined in other configurations, where technically possible.

What is claimed is:

1. An X-ray imaging system comprising:
    an X-ray source;
    an X-ray detector; and
    a collimator assembly coupled to the X-ray detector,
    wherein the X-ray detector comprises a plurality of detector modules arranged side-by-side and oriented towards the X-ray source, the detector modules being arranged side-by-side along a direction substantially orthogonal to the direction of incoming X-rays,
    wherein the collimator assembly includes a plurality of spaced apart collimator plates arranged side-by-side in a direction coinciding with the direction of the detector modules, and
    wherein the collimator assembly further comprises a physically stabilizing lateral support structure arranged in a lateral plane extending in a direction substantially orthogonal to the direction of incoming X-rays, wherein the physically stabilizing lateral support structure comprises at least one side plate having a plurality of openings therein and attached to at least part of a short side of at least a subset of the collimator plates.

2. The X-ray imaging system of claim 1, wherein the X-ray imaging system is a Computed Tomography (CT) imaging system.

3. The X-ray imaging system of claim 2, wherein the collimator plates are arranged side-by-side in the direction of the rotational axis of the CT imaging system, also denoted as a z-direction.

4. The X-ray imaging system of claim 2, wherein the collimator plates are arranged side-by-side in the angular direction of the CT imaging system, also denoted as an x-direction.

5. The X-ray imaging system of claim 1, wherein the physically stabilizing lateral support structure comprises a number of strips and/or wires extending in the lateral plane and attached to at least part of a short side of at least a subset of the collimator plates.

6. The X-ray imaging system of claim 1, wherein the physically stabilizing lateral support structure is formed as a fence and/or a grid attached to at least part of a short side of at least a subset of the collimator plates.

7. The X-ray imaging system of claim 1, wherein the at least one side plate having the plurality openings therein is a honeycomb-shaped plate.

8. The X-ray imaging system of claim 1, wherein the physically stabilizing lateral support structure comprises at least one side cover sheet attached to at least part of a short side of at least a subset of the collimator plates.

9. The X-ray imaging system of claim 1, wherein the physically stabilizing lateral support structure is arranged on both sides of the collimator plates.

10. The X-ray imaging system of claim 1, wherein the physically stabilizing lateral support structure includes or is made of Carbon Fiber Reinforced Polymers (CFRP).

11. The X-ray imaging system of claim 1, wherein the collimator assembly further comprises a top holding plate and a bottom holding plate to which the collimator plates are attached.

12. The X-ray imaging system of claim 10, wherein the top holding plate and the bottom holding plate are carbon caps.

13. The X-ray imaging system of claim 1, wherein the collimator assembly further comprises a hardened foam layer provided between at least a subset of the collimator plates.

14. The X-ray imaging system of claim 1, wherein at least a subset of the collimator plates are arranged for alignment with spaces or gaps defined between adjacent detector modules.

15. The X-ray imaging system of claim 1, wherein an X-ray attenuating assembly is arranged between at least a subset of the detector modules.

16. The X-ray imaging system of claim 15, wherein at least one of the collimator plates is provided as an extension of the X-ray attenuating assembly.

17. The X-ray imaging system of claim 15, wherein the X-ray attenuating assembly comprises at least one X-ray attenuating plate or sheet or anti-scatter foil.

18. The X-ray imaging system of claim 1, wherein each detector module has an array of detector elements extending in the direction of incoming X-rays and a direction orthogonal to both the direction of incoming X-rays and a main extension direction, and each of the collimator plates extends in the same directions.

19. The X-ray imaging system of claim 1, wherein the physically stabilizing lateral support structure is attached to at least part of a short side of at least a subset of the collimator plates by an adhesive.

\* \* \* \* \*